US007718193B2

(12) United States Patent
Stayton et al.

(10) Patent No.: US 7,718,193 B2
(45) Date of Patent: May 18, 2010

(54) TEMPERATURE- AND PH-RESPONSIVE POLYMER COMPOSITIONS

(75) Inventors: Patrick S. Stayton, Seattle, WA (US); Allan S. Hoffman, Seattle, WA (US); Xiangchun Yin, Seattle, WA (US); Lakeshia J. Taite, Seattle, WA (US); Jessica Garbern, Seattle, WA (US)

(73) Assignee: University of Washington, Seattle, WA (US)

( * ) Notice: Subject to any disclaimer, the term of this patent is extended or adjusted under 35 U.S.C. 154(b) by 5 days.

(21) Appl. No.: 11/687,522

(22) Filed: Mar. 16, 2007

(65) Prior Publication Data
US 2007/0224241 A1   Sep. 27, 2007

Related U.S. Application Data

(60) Provisional application No. 60/782,789, filed on Mar. 16, 2006.

(51) Int. Cl.
*A61K 9/14* (2006.01)
*A61K 31/74* (2006.01)

(52) U.S. Cl. .................... 424/487; 424/78.08

(58) Field of Classification Search ........... None
See application file for complete search history.

(56) References Cited

U.S. PATENT DOCUMENTS

| | | | |
|---|---|---|---|
| 4,657,543 A | 4/1987 | Langer | |
| 5,135,876 A | 8/1992 | Andrade | |
| 5,362,308 A | 11/1994 | Chien | |
| 5,451,411 A | 9/1995 | Gombotz | |
| 5,466,348 A | 11/1995 | Holm-Kennedy | |
| 5,501,584 A | 3/1996 | Yamamoto | |
| 5,521,291 A | 5/1996 | Curiel | |
| 5,547,932 A | 8/1996 | Curiel | |
| 5,569,364 A | 10/1996 | Hooper | |
| 5,599,908 A | 2/1997 | Raso | |
| 5,603,931 A | 2/1997 | Raso | |
| 5,609,590 A | 3/1997 | Herbig | |
| 5,656,609 A | 8/1997 | Wu | |
| 5,753,263 A | 5/1998 | Lishko | |
| 5,770,627 A | 6/1998 | Inoue | |
| 5,807,306 A | 9/1998 | Shapland | |
| 5,876,989 A | 3/1999 | Berg | |
| 5,939,453 A | 8/1999 | Heller | |
| 5,998,588 A | 12/1999 | Hoffman | |
| 6,165,509 A | 12/2000 | Hoffman | |
| 6,210,717 B1 | 4/2001 | Choi | |
| 6,426,086 B1 * | 7/2002 | Papahadjopoulos et al. . | 424/450 |
| 6,486,213 B1 | 11/2002 | Chen | |
| 6,835,393 B2 | 12/2004 | Hoffman | |
| 2001/0027072 A1 | 10/2001 | Mumick | |
| 2004/0239738 A1 * | 12/2004 | Watanabe ................... | 347/100 |
| 2005/0124728 A1 * | 6/2005 | Komatsu et al. ............ | 523/160 |

FOREIGN PATENT DOCUMENTS

| | | |
|---|---|---|
| EP | 0 693 508 A1 | 8/1995 |
| EP | 1 396 508 A1 | 10/2004 |
| WO | WO 00/43355 A1 | 7/2000 |
| WO | WO 2005021612 A1 * | 10/2005 |

* cited by examiner

*Primary Examiner*—Michael G Hartley
*Assistant Examiner*—Paul Dickinson
(74) *Attorney, Agent, or Firm*—Christensen O'Connor Johnson Kindness PLLC

(57) ABSTRACT

Temperature- and pH-responsive copolymer compositions, and drug delivery devices, conjugates, nanoparticles, and micelles that include the compositions.

18 Claims, 25 Drawing Sheets

(A)

TEMPERATURE- AND PH-RESPONSIVE POLYMER COMPOSITIONS

CROSS-REFERENCE TO RELATED APPLICATION

This application claims the benefit of U.S. Provisional Patent Application No. 60/782,789, filed Mar. 16, 2006, expressly incorporated herein by reference in its entirety.

STATEMENT OF GOVERNMENT LICENSE RIGHTS

This invention was made with government support under Grant Nos. EB2991 and EB000252, awarded by the National Institutes of Health. The Government has certain rights in the invention.

BACKGROUND OF THE INVENTION

Polymer systems that undergo phase transitions in response to environmental stimuli such as temperature and pH have been widely investigated for drug delivery, separations, and diagnostics applications. A key temperature-responsive class is based on alkyl acrylamide polymers, especially poly(N-isopropylacrylamide) (pNIPAAm), which undergoes a sharp coil-globule transition and phase separation at its lower critical solution temperature (LCST) in water. This spontaneous process is endothermic and is therefore driven by a gain in entropy associated with the release of hydrophobically-bound water molecules. The LCST of such thermally-sensitive polymers can be tuned to a desired temperature range by copolymerization with a more hydrophilic comonomer (which raises the LCST) or a more hydrophobic comonomer (which lowers the LCST).

pH-Sensitive monomers may also be copolymerized with NIPAAm. For these copolymers, the phase separation can also be triggered by a change in the pH at specific temperatures, such as 37° C. Readily available carboxylic acid monomers, such as acrylic acid (AA) or methacrylic acid (MAA), have been copolymerized with NIPAAm using traditional free radical polymerization techniques to form random copolymers with both temperature- and pH-responsive properties. However, the LCSTs of copolymers increase rapidly with increasing acrylic acid comonomer contents at all pH ranges because acrylic acid is intrinsically more hydrophilic than NIPAAm in both the protonated and unprotonated states. In addition, the critical transitions of pH responsive copolymers of NIPAAm with acrylic acid and methacrylic acid are usually below pH 5.0 due to the low $pK_a$ values of poly(acrylic acid) and poly(methacrylic acid). Because of this, it has been a general challenge to design NIPAAm copolymers capable of responding to the physiologically-relevant pHs between 5.0 and 7.4.

The properties of NIPAAm copolymers with the hydrophobic acidic monomers 4-pentenoic acid, 6-acrylaminohexanoic acid, and N-acryloyl-L-phenylalanine have been previously reported. The LCSTs of these copolymers decreased at pH 4.0 and increased at pH 7.4 with increasing the content of comonomer 4-pentenoic acid or 6-acrylaminohexanoic acid.

Hydrogels can be made from stimuli-responsive polymers. Stimuli-responsive hydrogels have earned the reputation of "smart materials" because they are able to change abruptly their volume or properties in response to environmental conditions such as temperature, pH, light, and biomolecules. Among the "smart hydrogel materials," particular attention has been paid to temperature-sensitive poly(N-isopropylacrylamide) (pNIPAAm) hydrogels. Like certain temperature-responsive polymers, pNIPAAm hydrogels undergo an abrupt phase transition in water upon heating above 32° C., when the hydrophilic extended coils collapse into hydrophobic globules causing the gels to shrink and expel most of the absorbed water. Such phase transition behavior is thermoreversible. Some copolymer hydrogels of NIPAAm and acidic (e.g., acrylic acid, methacrylic acid) or basic comonomers are known to be both pH-sensitive and temperature-sensitive. These dual pH/temperature responsive hydrogels have a variety of applications in many fields including controlled drug delivery systems, chromatographic separation, cell culture, microfluidic actuators/valves, and biosensors.

Readily available carboxylic acid monomers, such as acrylic acid or methacrylic acid, have been copolymerized with NIPAAm using free radical polymerization to form copolymer hydrogels with dual temperature- and pH-responsive properties. However, the critical transitions of pH/temperature responsive NIPAAm and acrylic acid copolymer hydrogels are usually below pH 4.0 due to the low pKa values of poly(acrylic acid) ($pK_a \approx 4.25$). One serious concern regarding these hydrogels is that many biomolecules, such as peptides and protein, are not stable at low pH. In addition, an increase of acrylic acid content in the NIPAAm copolymer hydrogel could reduce or even eliminate the temperature sensitivity because the hydrophilic acrylic acid comonomer units break pNIPAAm chain sequences into short, uncooperative network segments and, subsequently, weak thermally-driven hydrophobic aggregation of the pNIPAAm chain. Therefore, NIPAAm and acrylic acid copolymer hydrogels cannot show the abrupt and large volume phase transition in an ideal pH range as required in many applications such as microfluidic actuators/valves and drug delivery devices.

Despite the development of temperature- and pH-sensitive copolymers and hydrogels, a need exists for temperature- and pH-sensitive polymer compositions including temperature- and pH-sensitive copolymers and hydrogels having phase transitions at operationally useful temperature and physiological pH (about 5.0 to about 7.4). The present invention seeks to fulfill this need and provides further related advantages.

SUMMARY OF THE INVENTION

The present invention provides polymer compositions that are responsive to both temperature and pH. The polymer compositions of the invention include copolymers derived from copolymerization of a pH-responsive monomer and a temperature-responsive monomer.

In one aspect, the present invention provides a temperature- and pH-responsive random copolymer. In one embodiment, the random copolymer, comprises:
 (a) temperature-responsive repeating units, wherein the repeating unit is an N-alkylacrylamide repeating unit; and
 (b) pH-responsive repeating units, wherein the repeating unit is a C2-C8 alkylacrylic acid repeating unit.

In one embodiment, the copolymer exhibits a phase transition at a pH of from about pH 5.0 to about pH 7.4.

In one embodiment, the N-alkylacrylamide is a C3-C8 alkyl N-alkylacrylamide. In one embodiment, the N-alkylacrylamide is N-isopropylacrylamide.

In one embodiment, the C2-C8 alkylacrylic acid is a C2-C8 n-alkylacrylic acid. In one embodiment, the C2-C8 alkylacrylic acid is selected from the group consisting of ethylacrylic acid, n-propylacrylic acid, and n-butylacrylic acid. In one embodiment, the C2-C8 alkylacrylic acid is n-propylacrylic acid.

In one embodiment, the N-alkylacrylamide is N-isopropylacrylamide and the C2-C8 alkylacrylic acid is propylacrylic acid.

In one embodiment, the pH-responsive repeating units are present in the copolymer in an amount from about 1 to about 50 weight percent.

In one embodiment, the copolymer has a molecular weight of from about 5,000 to about 40,000.

In another aspect of the invention, a temperature- and pH-responsive hydrogel is provided. In one embodiment, the hydrogel comprises a crosslinked copolymer, wherein the copolymer comprises:
  (a) temperature-responsive repeating units, wherein the repeating unit is an N-alkylacrylamide repeating unit; and
  (b) pH-responsive repeating units, wherein the repeating unit a C2-C8 alkylacrylic acid repeating unit.

In one embodiment, the hydrogel exhibits a phase transition at a pH of from about pH 5.0 to about pH 7.4.

In one embodiment, the N-alkylacrylamide is a C3-C8 alkyl N-alkylacrylamide. In one embodiment, the N-alkylacrylamide is N-isopropylacrylamide.

In one embodiment, the C2-C8 alkylacrylic acid is a C2-C8 n-alkylacrylic acid. In one embodiment, the C2-C8 alkylacrylic acid is selected from the group consisting of ethylacrylic acid, n-propylacrylic acid, and n-butylacrylic acid. In one embodiment, the C2-C8 alkylacrylic acid is n-propylacrylic acid.

In one embodiment, the N-alkylacrylamide is N-isopropylacrylamide and the C2-C8 alkylacrylic acid is propylacrylic acid.

In one embodiment, the pH-responsive repeating units are present in the copolymer in an amount from about 1 to about 50 weight percent.

In one embodiment, the hydrogel further comprises one or more therapeutic drugs or diagnostic agents. In one embodiment, the therapeutic drug or diagnostic agent is selected from the group consisting of a protein, a peptide, and a nucleic acid.

In one embodiment, the hydrogel further comprises a sugar. In one embodiment, the sugar is trehalose.

In another aspect, the present invention provides a temperature- and pH-responsive block copolymer. In one embodiment, the block copolymer, comprises:
  (a) a first block comprising a random copolymer comprising:
    (i) temperature-responsive repeating units, wherein the repeating unit is an N-alkylacrylamide repeating unit; and
    (ii) pH-responsive repeating units, wherein the repeating unit a C2-C8 alkylacrylic acid repeating unit; and
  (b) a second hydrophobic block.

In one embodiment, the copolymer exhibits a phase transition at a pH of from about pH 5.0 to about pH 7.4.

In one embodiment, the N-alkylacrylamide is a C3-C8 alkyl N-alkylacrylamide. In one embodiment, the N-alkylacrylamide is N-isopropylacrylamide.

In one embodiment, the C2-C8 alkylacrylic acid is a C2-C8 n-alkylacrylic acid. In one embodiment, the C2-C8 alkylacrylic acid is selected from the group consisting of ethylacrylic acid, n-propylacrylic acid, and n-butylacrylic acid. In one embodiment, the C2-C8 alkylacrylic acid is n-propylacrylic acid.

In one embodiment, the N-alkylacrylamide is N-isopropylacrylamide and the C2-C8 alkylacrylic acid is propylacrylic acid.

In one embodiment, the pH-responsive repeating units are present in the random copolymer in an amount from about 1 to about 20 weight percent. In one embodiment, the random copolymer has a molecular weight of from about 5,000 to about 20,000.

In one embodiment, the block copolymer has a molecular weight of from about 15,000 to about 60,000.

In one embodiment, the hydrophobic block is selected from the group consisting of a polystyrene, a poly(methylmethacrylate), a poly(ethylacrylate), a poly(butylacrylate), a poly(glycotide-co-lactide), and a polyoxyethylene-polyoxypropylene copolymer. In one embodiment, the hydrophobic block is selected from the group consisting of a poly(ethylacrylate) and a poly(butylacrylate).

In another aspect, the present invention provides a temperature- and pH-responsive drug delivery device. In one embodiment, the drug delivery device comprises the random copolymer of the invention described above and one or more therapeutic drugs or diagnostic agents. In one embodiment, the drug delivery device comprises the hydrogel of the invention described above and one or more therapeutic drugs or diagnostic agents. In one embodiment, the drug delivery device comprises the block copolymer of the invention described above and one or more therapeutic drugs or diagnostic agents.

In another aspect, the present invention provides a temperature- and pH-responsive conjugate. In one embodiment, the conjugate comprises the random copolymer of the invention described above and one or more therapeutic drugs or diagnostic agents. In one embodiment, the conjugate comprises the hydrogel of the invention described above and one or more therapeutic drugs or diagnostic agents. In one embodiment, the conjugate comprises the block copolymer of the invention described above and one or more therapeutic drugs or diagnostic agents.

In one aspect, the present invention provides a temperature- and pH-responsive modified nanoparticle. In one embodiment, the modified nanoparticle comprises the random copolymer of the invention described above attached to a nanoparticle. In one embodiment, the modified nanoparticle comprises the hydrogel of the invention described above attached to a nanoparticle. In one embodiment, the modified nanoparticle comprises the block copolymer of the invention described above attached to a nanoparticle. The nanoparticles of the invention can further include one or more therapeutic drug or diagnostic agent.

In another aspect, the present invention provides a temperature- and pH-responsive micelle useful for reagent delivery. In one embodiment, the micelle comprises the block copolymer of the invention described above and one or more therapeutic drugs or diagnostic agents.

In other aspects, methods for making and using the polymer compositions are also provided.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

DETAILED DESCRIPTION OF THE INVENTION

Figure 1A:
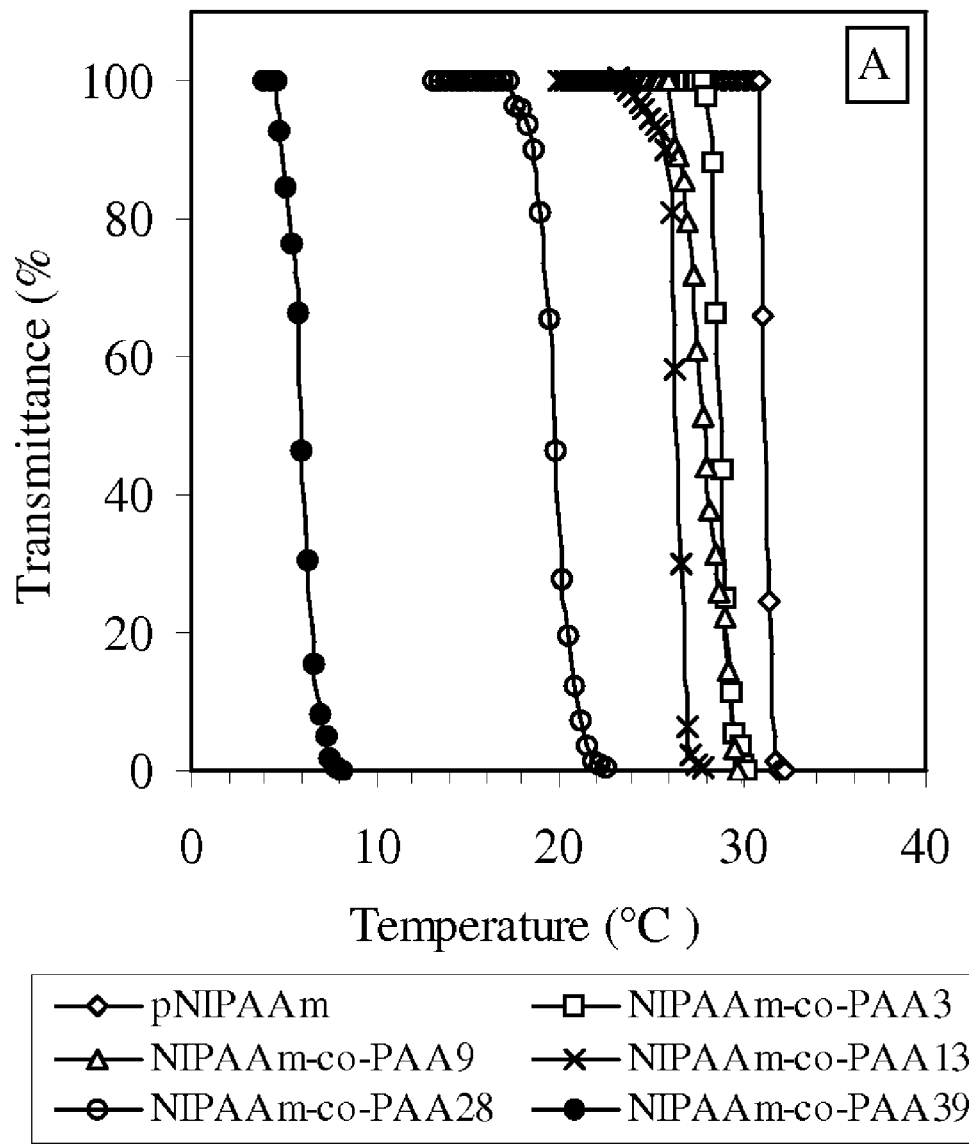
FIGS. 1A and 1B are transmission versus temperature curves comparing phase transitions for solutions of representative NIPAAm-co-PAA copolymers of the invention at pH 5.0 and pH 6.5, respectively, as measured by the cloud point method.

The present invention provides polymer compositions that are responsive to both temperature and pH. The polymer compositions of the invention include copolymers derived from copolymerization of a pH-responsive monomer and a temperature-responsive monomer. The pH-responsive monomer imparts reversible transitions between hydrophilic and hydrophobic states to the polymer composition. The temperature-responsive monomer imparts reversible transitions between expanded and contracted states to the polymer compositions.

The choice of the alkylacrylic acid monomer, the ratio of the pH- and temperature-monomers, and the molecular weight of the product polymer affects two of the polymer's properties. The first is the pKa which describes the pH at which the polymer is in an expanded versus contracted (or collapsed) state. The second is the polymer's temperature dependence of the expanded versus collapse transitions. By choice of the alkylacrylic acid monomer, the ratio of the monomers, and the polymer's molecular weight small pH changes or hydration events trigger expansion or contraction (or collapse) at a given temperature, or, at a particular pH, small temperature changes or hydration can trigger the expansion or contraction.

Because the polymer compositions of the invention exhibit sharp and tunable responses to both temperature and pH, the compositions can be used to conjugate to recognition elements such as proteins or nucleic acids to reversibly capture diagnostic targets for purification and/or concentration, to reversibly form nanoparticles to purify and/or concentrate diagnostic targets. The polymer compositions can also be used as molecular switches to provide sharp pH and/or temperature control of protein activity.

The polymer compositions can also be used in stimuli-responsive drug or diagnostic reagent delivery systems, where release of reagents or drugs can be stimulated by hydration or by small changes in pH or temperature. The compositions can be used for storage and release of bioanalytical reagents in diagnostic and microfluidic devices, or for controlled delivery of therapeutics.

Temperature- and pH-Responsive Random Copolymers. In one aspect, the polymer composition of the invention is a random copolymer having both pH- and temperature-responsiveness.

In one aspect, the present invention provides a temperature- and pH-responsive random copolymer. In one embodiment, the random copolymer, comprises:
(a) temperature-responsive repeating units, wherein the repeating unit is an N-alkylacrylamide repeating unit; and
(b) pH-responsive repeating units, wherein the repeating unit is a C2-C8 alkylacrylic acid repeating unit.

In one embodiment, the N-alkylacrylamide is a C3-C8 alkyl N-alkylacrylamide. As used herein, the term "C3-C8 alkyl N-alkylacrylamide" refers to an N-alkylacrylamide in which the alkyl group is a C3-C8 alkyl group. The C3-C8 alkyl group may be a straight chain or branched alkyl group having from 3 to 8 carbon atoms. A representative N-alkylacrylamide is N-isopropylacrylamide.

As used herein, the term "C2-C8 alkylacrylic acid" refers to an alkylacrylic acid in which the alkyl group is a C2-C8 alkyl group. The C2-C8 alkyl group may be a straight chain or branched alkyl group having from 2 to 8 carbon atoms. In one embodiment, the C2-C8 alkylacrylic acid is a C2-C8 n-alkylacrylic acid. Representative C2-C8 alkylacrylic acids include ethylacrylic acid (EAA), n-propylacrylic acid (PAA), and n-butylacrylic acid (BAA). In one embodiment, the C2-C8 alkylacrylic acid is n-propylacrylic acid.

In one embodiment, the N-alkylacrylamide is N-isopropylacrylamide and the C2-C8 alkylacrylic acid is propylacrylic acid.

on the LCST than the polar carboxylic acid group at those conditions. An increase of pH led to a significant increase in LCST of the copolymers due to the ionization of the —COOH group. The LCSTs were studied as a function of copolymer composition over the pH range from 5.0 to 7.0.

Figure 1B:
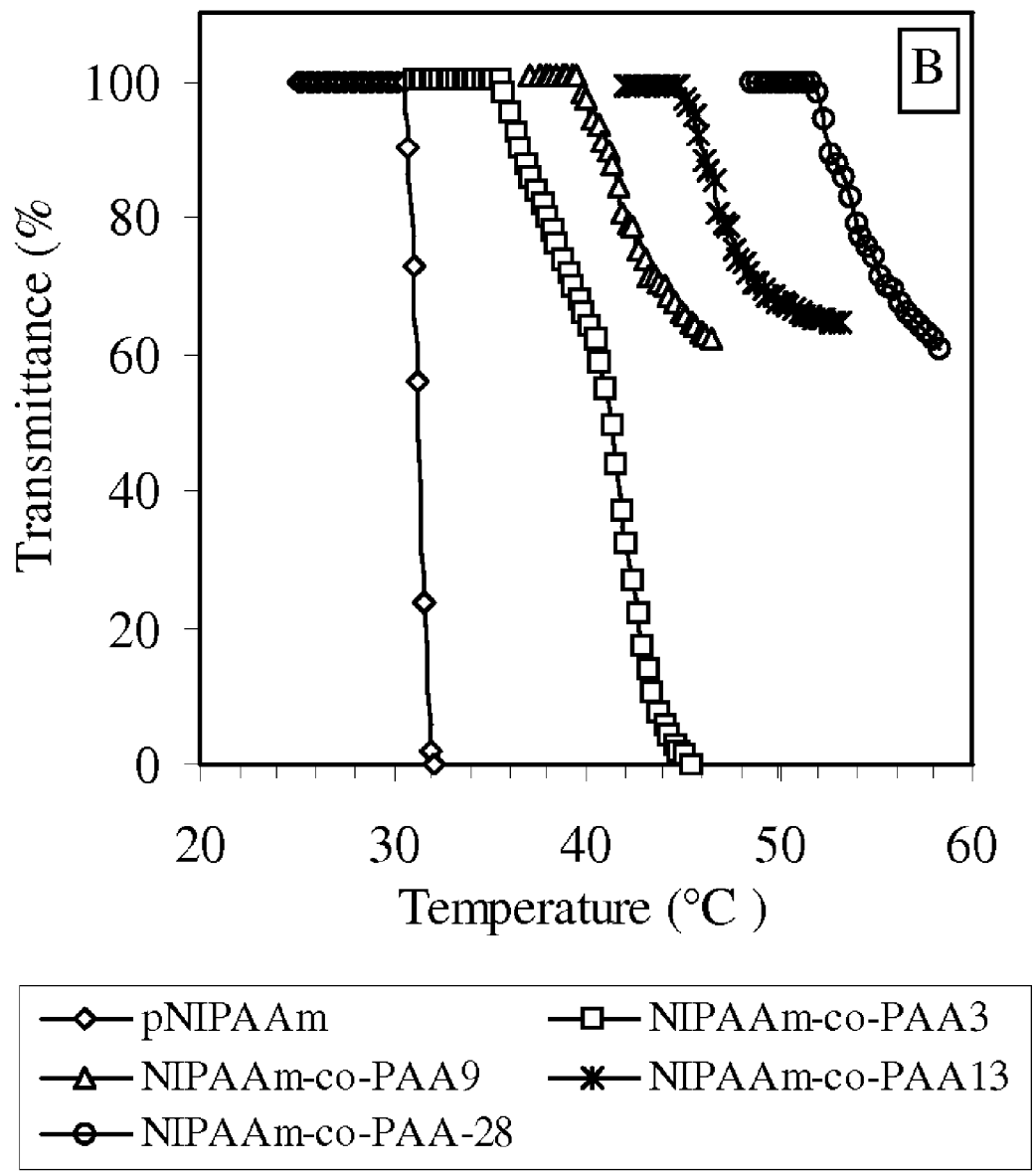

FIGS. 1A and 1B show typical transmittance versus temperature curves for representative copolymers of the invention with varied compositions at pH 5.0 and 6.5, respectively. The combination of pH-responsive PAA and thermo-responsive NIPAAm in the copolymer leads to a polymer that responds sharply to both pH and temperature.

Referring to FIGS. 1A and 1B, "pNIPAAm" refers to a poly(N-isopropylacrylamide); "NIPAAm-co-PAA3" refers to a representative N-isopropylacrylamide (NIPAAm)-propylacrylic acid (PAA) copolymer of the invention including 2.6 mole percent propylacrylic acid; "NIPAAm-co-PAA9" refers to a representative N-isopropylacrylamide (NIPAAm)-propylacrylic acid (PAA) copolymer of the invention including 8.8 mole percent propylacrylic acid; "NIPAAm-co-PAA13" refers to a representative N-isopropylacrylamide (NIPAAm)-propylacrylic acid (PAA) copolymer of the invention including 13.0 mole percent propylacrylic acid; "NIPAAm-co-PAA28" refers to a representative N-isopropylacrylamide (NIPAAm)-propylacrylic acid (PAA) copolymer of the invention including 27.8 mole percent propylacrylic acid; and "NIPAAm-co-PAA39" refers to a representative N-isopropylacrylamide (NIPAAm)-propylacrylic acid (PAA) copolymer of the invention including 39.2 mole percent propylacrylic acid. The preparations and characterization of these copolymers is described in Example 1 and summarized in Table 1.

TABLE 1

Preparation and Characterization of N-isopropylacrylamide-co-propylacrylic acid (NIPAAm-co-PAA) copolymers using RAFT copolymerization.[a]

| Polymer | PAA amount (mol %) | | [monomer]$_0$ [CTA]$_0$, + 2 [AIBN]$_0$ | Yield (wt %) | $M_n$,[d] (theor) | $M_n$[e] (expt) | $M_w/M_n$ |
|---|---|---|---|---|---|---|---|
| | in feed | in polymer | | | | | |
| NIPAAm | — | — | 200 | 86.0 | 22,900 | 32,500 | 1.08 |
| NIPAAm-co-PAA3 | 2.0 | 2.6[b]   2.3[c] | 200 | 80.5 | 18,200 | 27,300 | 1.16 |
| NIPAAm-co-PAA9 | 5.0 | 8.8   8.5 | 200 | 79.2 | 17,900 | 23,400 | 1.20 |
| NIPAAm-co-PAA13 | 10.0 | 13.0   12.6 | 200 | 68.4 | 15,500 | 21,700 | 1.20 |
| NIPAAm-co-PAA28 | 20.0 | 27.8   26.2 | 200 | 45.4 | 10,300 | 15,000 | 1.18 |
| NIPAAm-co-PAA39 | 30.0 | 39.2   35.6 | 400 | 30.4 | 13,700 | 19,200 | 1.28 |

[a]Polymerization was carried out at 60° C. for 17 h at 50 wt/v % monomer in methanol, 2,2'-azobis(isobutyronitrile) (AIBN) as initiator and 2-dodecylsulfonylthiocarbonylsulfonyl-2-methyl propionic acid as chain transfer agent (CTA). [CTA]0/[AIBN]0 = 5.
[b]Estimated from 1H NMR.
[c]Estimated from potential titration.
[d]Mn (theor) = conversion × MWmonomer × [M]0/([CTA] + 2[AIBN]).
[e]Determined by GPC in DMF containing 0.01 mol L−1 LiCl at 60° C. (poly(methyl methacrylate) standard).
[f]Polymerization time, 48 h.

In one embodiment, the pH-responsive repeating units are present in the copolymer in an amount from about 1 to about 50 weight percent.

In one embodiment, the copolymer has a molecular weight of from about 5,000 to about 40,000.

The phase transition properties of the polymer compositions of the invention described herein were measured by the cloud point method. For representative copolymers of the invention, NIPAAm-co-PAA copolymers, at slightly acidic conditions, the lower critical solution temperature (LCST) decreased with increase in PAA content, which suggests that the hydrophobic propyl group of PAA has a greater influence Referring to Table 1, the polymer yield decreased with increasing PAA in the feed. With as much as 30 mol % PAA in the monomer feed, the polymerization required higher total monomer concentration in the feed and longer polymerization times to yield polymers with similar chain lengths to those obtained in polymerizations with less that 10 mol % PAA feed. The polymerization reactivity of α-alkylacrylic acid monomers, such as PAA, is relatively low due to the steric hindrance of the growing chain end for chain propagation. In addition, polymers made from such monomers have low ceiling temperatures, where the polymerization equilibrium is reversed, i.e., from growing chain polymer back to monomer. Homopolymerization of ethylacrylic acid or propylacrylic acid worked only under bulk polymerization conditions with low polymer yields. Due to the wide application of these hydrophobic poly(carboxylic acids), copolymerizing α-alkylacrylic acid with other monomers like NIPAAm may offer a facile approach to copolymers with versatile structures and applications.

The LCST of thermo-responsive polymers is attributed to a change in the hydrophilic/hydrophobic balance of the polymers with respect to the hydrophobic and H-bond interactions of water molecules with the polymer chain. At low temperatures, strong H-bonding interactions between polar groups and water lead to good solubility of the polymer, which is opposed by the hydration of apolar groups. The water surrounding the apolar groups is in a low entropy state relative to free water, leading to an entropic penalty. As the apolar surface area of the polymer increases this entropic penalty will increase, and the LCST will decrease.

Figure 2:
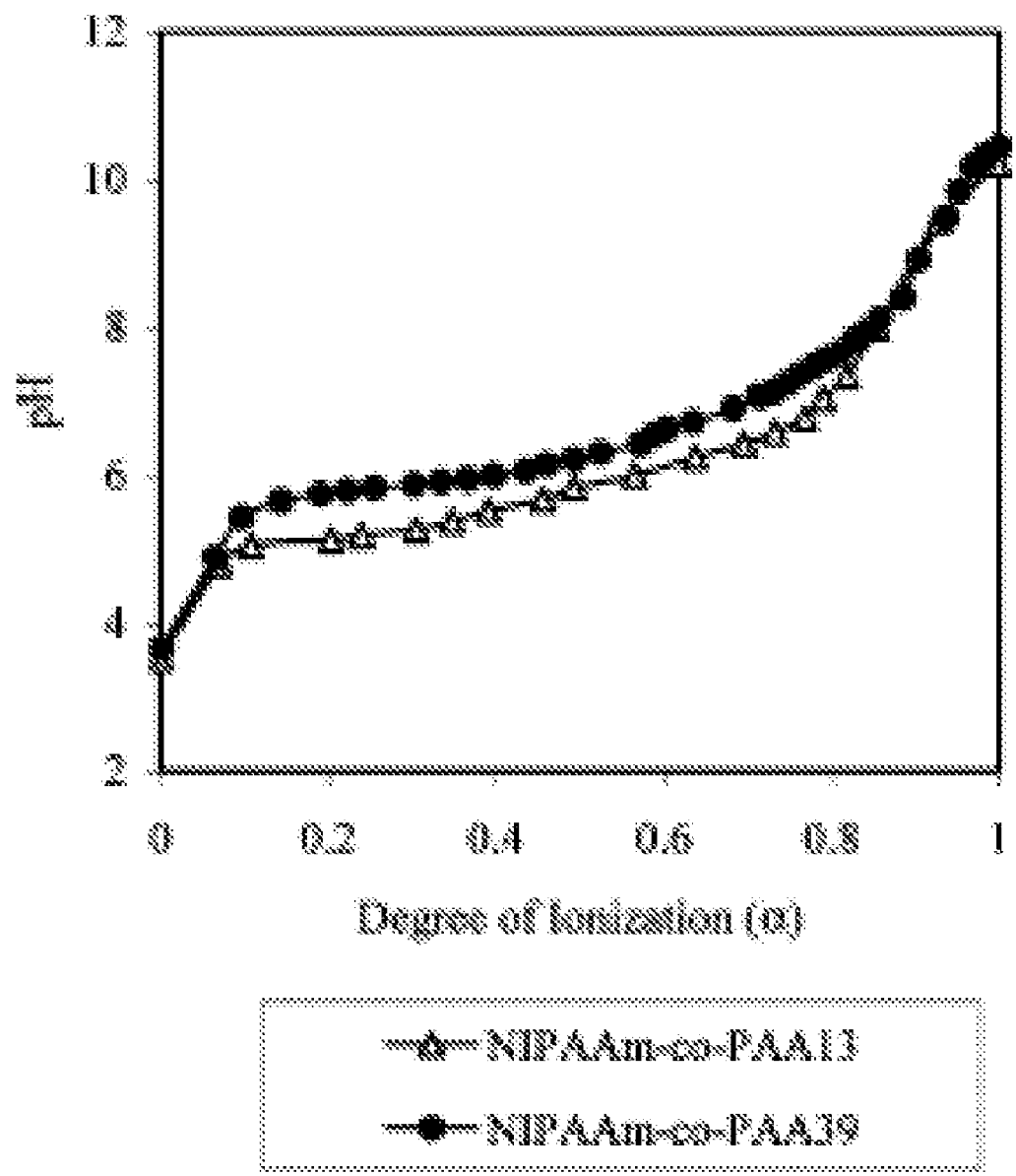
FIG. 2 is a titration graph illustrating pH versus degree of ionization for solutions of representative NIPAAm-co-PAA copolymers of the invention: NIPAAm-co-PAA13 and NIPAAm-co-PAA39 (10 mg/ml 0.15 mol $L^{-1}$ NaCl at room temperature.

The LCST values of NIPAAm-co-PAA copolymers decrease with increasing PAA contents at pH 5 (FIG. 1A). In contrast, they increase with an increase of PAA content at pH 6.5, NIPAAm-co-PAA39 does not exhibit an LCST in the experimental temperature range (0-100° C.) (FIG. 1B). FIG. 2 shows titration curves of NIPAAm-co-PAA13 and NIPAAm-co-PAA39 at room temperature. The $pK_a$ values of these copolymers are 5.9 and 6.2, respectively. The copolymers are less than 10% ionized at pH 5.0, while about 60% ionized at pH 6.5. PAA is hydrophobic in the acidic form, and causes the LCST of PNIPAAm to decrease. It is also possible that the —COOH group of PAA will H-bond with the —CONH group of NIPAAm at the lower pHs, and that could also contribute to the lowering of its LCST. This effect was seen in graft copolymers of pNIPAAm-g-p(acrylic acid). At higher pH values, the copolymer clearly becomes much more ionized, leading to the increase in LCST. Upon ionization at higher pH values, the copolymer chains will also expand due to the electrostatic repulsion between charged sites along the backbone and thus lower the polymer-polymer interactions.

Referring to FIGS. 1A and 1B, the phase transition curves of NIPAAm-co-PAA copolymer solutions are sharp at pH 5.0 (FIG. 1A), while the transmittance decreases much more gradually at pH 6.5 (FIG. 1B) and does not reach 0% over a wide temperature range, especially for polymers with high PAA contents, due to the ionization of PAA units. As more of the PAA monomer units of the copolymer chains are ionized, their hydrophilicity will interfere with the thermally-induced phase separation tendencies of the NIPAAm chain sequences, and subsequently weaken the aggregation of pNIPAAm chain segments. In addition, the aggregation of polymer chains into large aggregates may also be decreased due to the ionic stabilization by ionized PAA units of smaller aggregates in the solution.

Table 2 shows the comparison of LCSTs of N-isopropylacrylamide-co-acrylic acid (NIPAAm-co-AA), N-isopropylacrylamide-co-methacrylic acid (NIPAAm-co-MAA), and N-isopropylacrylamide-co-propylacrylic acid (NIPAAm-co-PAA) copolymers with similar NIPAAm contents at different pHs. Because the $pK_a$ of the polymer compositions of the invention can be tuned to fall around neutral pH, these polymer compositions can be designed to have phase transitions triggered around physiological pH, or at slightly acidic pH values that fall within the values of acidic gradients found in biological systems. This behavior is notably different from the previously described polymer compositions utilizing acrylic acid (AA) or methylacrylic acid (MA) monomers. NIPAAm-co-AA with 10 mol % AA has higher LCST than homoNIPAAm even at pH 4.0 due to the intrinsically hydrophilic AA units and its low pKa value. PolyMAA has relative higher pKa value and it is hydrophobic at acidic conditions. The LCST of NIPAAm-co-MAA with 11.5 mol % MAA is lower than that of homoNIPAAm at pH 4.0, but higher at pH 5.0. No LCST was detected at pH≧6.0. In contrast, the hydrophobic PAA causes the LCST of polyNIPAAm to decrease at pH up to 5.5. At pH 6.0, this copolymer still exhibits LCST behavior at temperature below physiological temperature (37° C.).

TABLE 2

The LCSTs of N-isopropylacrylamide-co-acrylic acid (NIPAAm-co-AA), N-isopropylacrylamide-co-methacrylic acid (NIPAAm-co-MAA) and N-isopropylacrylamide-co-propylacrylic acid (NIPAAm-co-PAA) copolymers with similar NIPAAm contents at different pHs.[a]

| pH | NIPAAm-co-AA | NIPAAm-co-MAA | NIPAAm-co-PAA13 |
|---|---|---|---|
| 4.0 | 34.3° C. | 29.0° C. | not soluble above 0° C. |
| 5.0 |  | 36.7° C. | 23.0° C. |
| 5.5 |  | 63.8° C. | 27.1° C. |
| 6.0 |  | no LCST | 34.2° C. |
| 6.5 |  | no LCST | 46.0° C. |

[a]NIPAAm-co-AA has 10 mol % AA and the LCST was from Olea, A. F.; Thomas, J. K. Macromolecules 22: 1165-1169, 1989. NIPAAm-co-MAA with 11.5 mol % MAA was prepared by RAFT polymerization, and its $M_n$ and PDI were 28,100 and 1.21, respectively.

NIPAAm-co-AA with 10 mol % AA has higher LCST than homoNIPAAm even at pH 4.0 due to the intrinsically hydrophilic AA units and its low $pK_a$ value. PolyMAA has relative higher $pK_a$ value and it is hydrophobic at acidic conditions. The LCST of NIPAAm-co-MAA with 11.5 mol % MAA is lower than that of homoNIPAAm at pH 4.0, but higher at pH 5.0. No LCST was detected at pH≧6.0. In contrast, the hydrophobic PAA causes the LCST of polyNIPAAm to decrease at pH up to 5.5. At pH 6.0, this copolymer still exhibits LCST behavior at temperature below physiological temperature (37° C.).

Figure 3A:
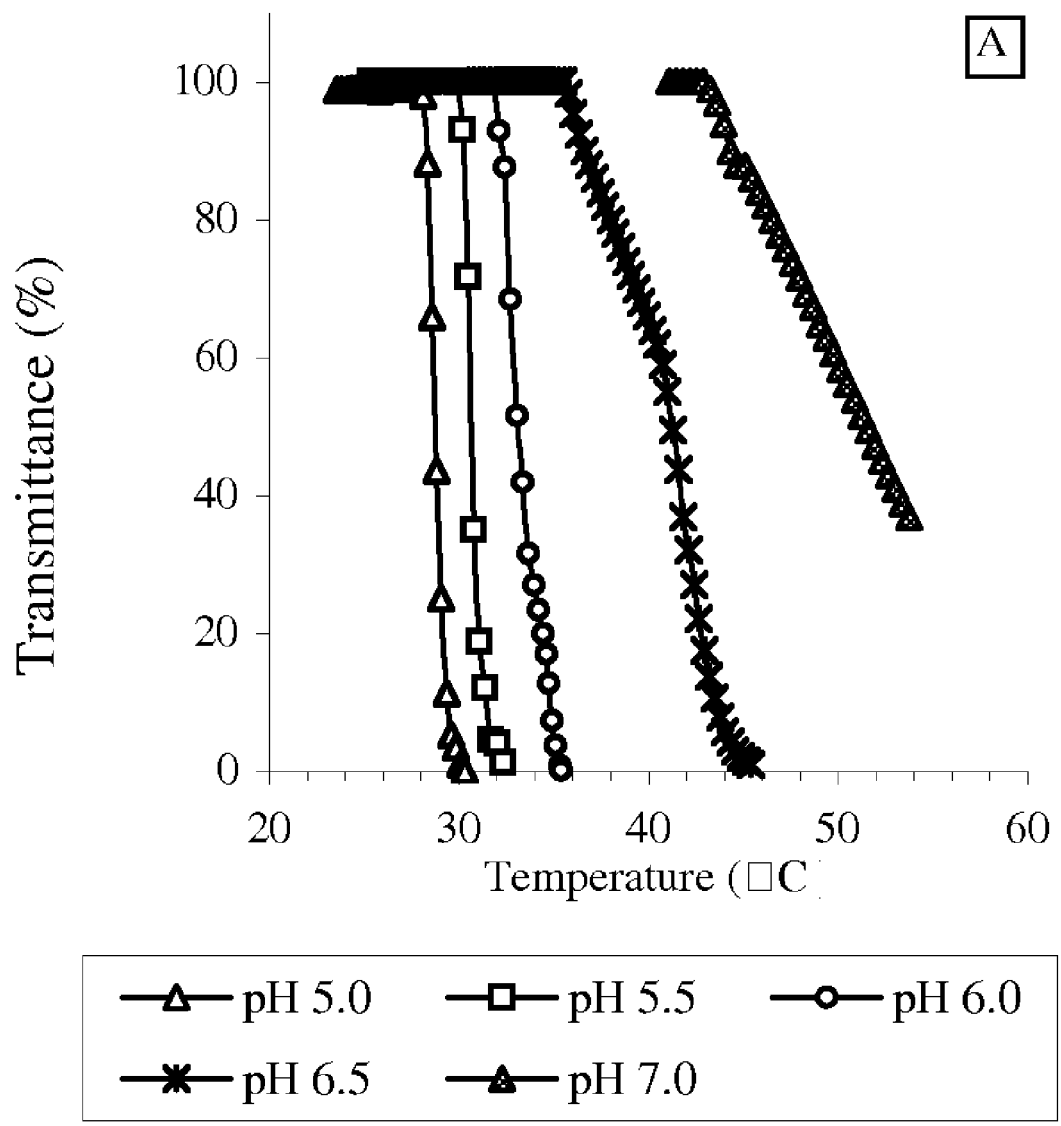
FIGS. 3A and 3B are transmission versus temperature curves comparing phase transitions for solutions of representative NIPAAm-co-PAA copolymers of the invention: NIPAAm-co-PAA3 at pH 5.0, 5.5, 6.0, 6.5, and 7.0 (FIG. 3A); and NIPAAm-co-PAA39 at pH 5.0, 5.5, and 6.0 (FIG. 3B)
Figure 3B:
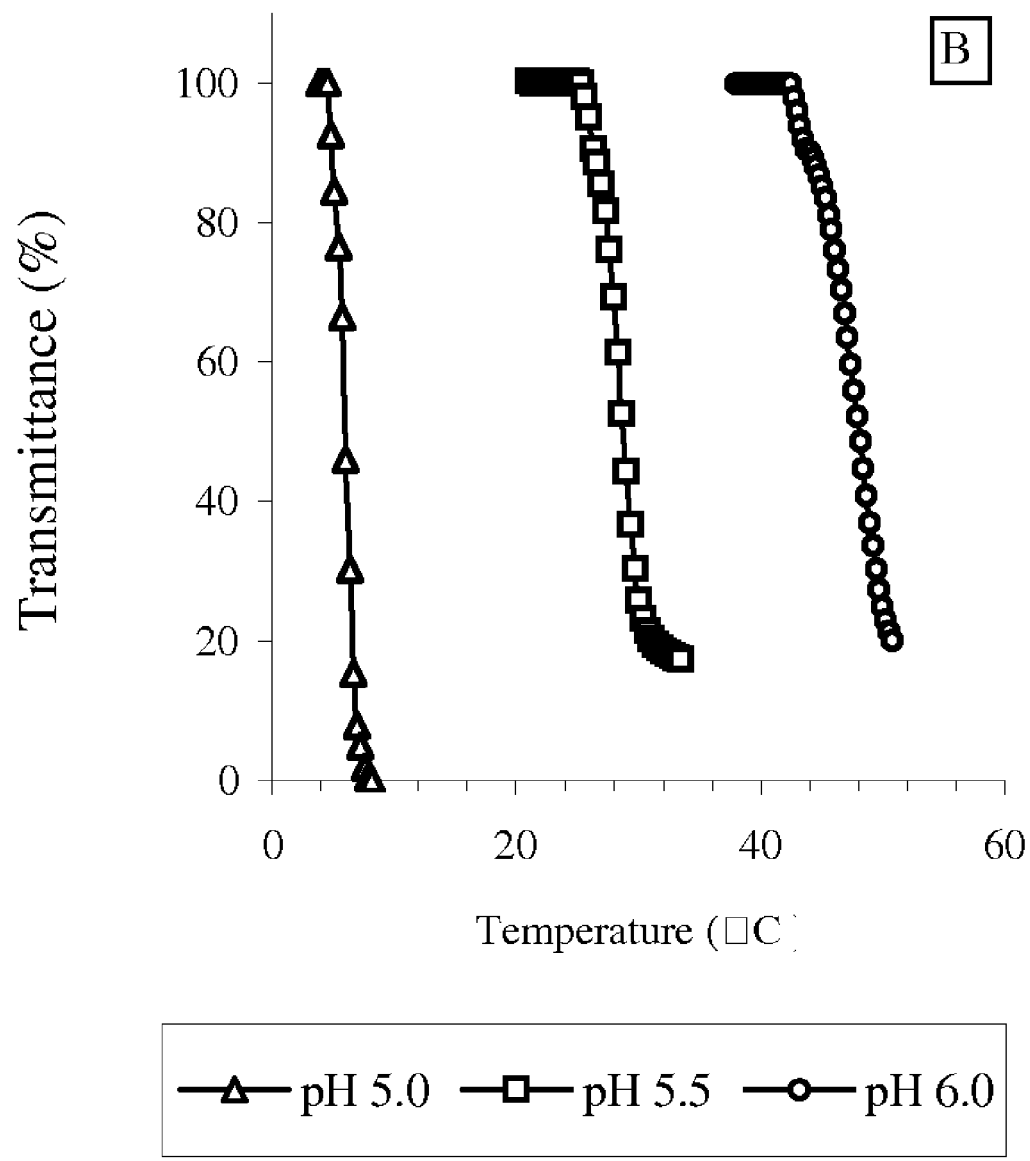
Figure 4:
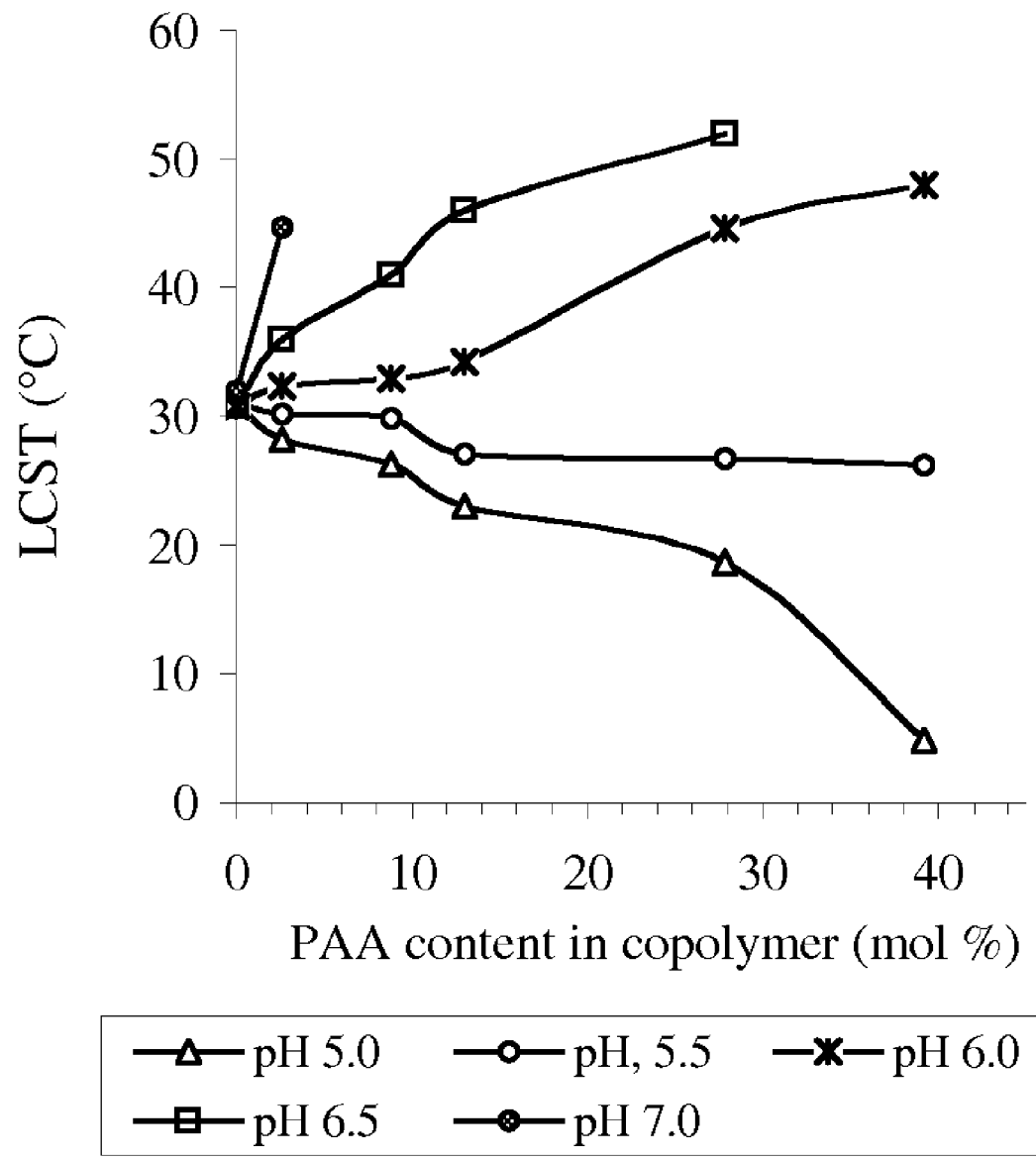
FIG. 4 is a graph illustrating LCSTs of 0.2 wt % poly(N-isopropylacrylamide-co-propylacrylic acid) (NIPAAm-co-PAA) solutions with different PAA contents at different pHs as measured by the cloud point method.

The influence of pH on the LCSTs of varying NIPAAm-co-PAA copolymer compositions from pH 5.0 to 7.0 is shown in FIGS. 3 and 4). The phase transition curves of the copolymers with about 3 mol % PAA are shown in FIG. 3A. At pH 5.0, the LCST is about 28° C., which is lower than that of homopolymer pNIPAAm (31° C.) in the same solution. The LCST increases to about 45° C. at pH 7.0 due to the ionization of PAA units. For copolymers with 39 mol % PAA, the LCST is influenced by pH more dramatically: for example, LCSTs are 4.8° C. at pH 5.0, 26.2° C. at pH 5.5, and 48° C. at pH 6.0. The LCST disappears at and above pH 6.5, indicating that the ionized PAA units significantly reduce the effect of any hydrophobically bound water, and convey sufficient solubility to offset the temperature-sensitivity of NIPAAm components.

Referring to FIG. 4, both the percentage of PAA and the pH are important to the shift in LCST. At both low and high PAA contents, a small increase in pH can cause dramatic increases in the LCST. Thus, the LCST can be adjusted to any desired range at a particular pH value (such as endosomal pH) by changing the PAA content of the copolymer. The temperature-responsive NIPAAm-co-PAA copolymer is triggered under a small pH change window as sufficient PAA units switch from a hydrophobic state to an ionized state at defined regions between pH 5.0-7.0. This remarkable pH/temperature responsiveness could be useful in a variety of biomedical applications. In molecular switching applications, the expansion and collapse of these chains could be controlled to occur more sharply over a small pH range nearer to neutral pH, which is important to protect protein stability. The combined pH/temperature responsiveness could also be used to enhance drug delivery where acidic pH gradients are encountered in the body.

Figure 5:
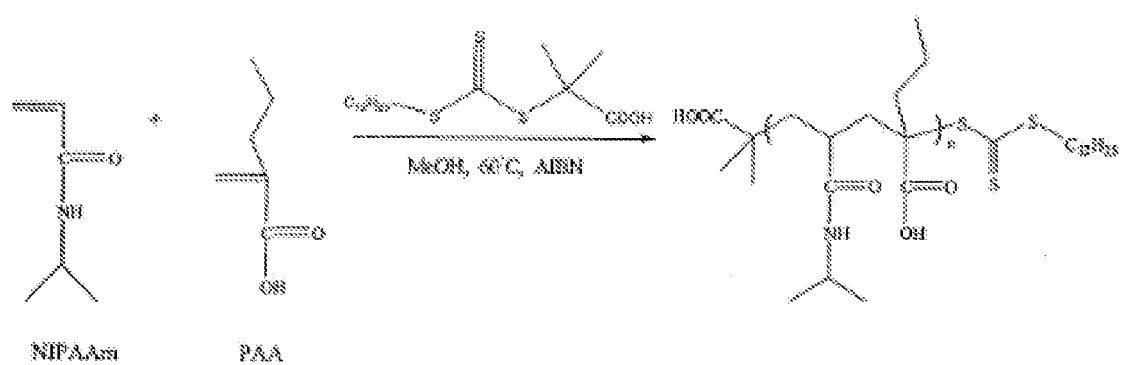
FIG. 5 is a schematic illustration of the RAFT copolymerization synthesis of representative NIPAAm-co-PAA copolymers of the invention.

The copolymer compositions of the invention can be prepared by reverse addition fragment chain transfer (RAFT) polymerization. In one embodiment, the NIPAAm-co-PAA copolymers of the invention are prepared by RAFT copolymerization of varying ratios of NIPAAm and PAA monomers in methanol using AIBN as an initiator and DMP as the chain transfer agent (CTA) (a trithiocarbonate, 2-dodecylsulfonylthiocarbonylsulfonyl-2-methyl propionic acid). Five NIPAAm-co-PAA copolymers with different PAA contents were prepared as illustrated schematically in FIG. 5.

The RAFT copolymerization proceeds in a controlled way with a $[CTA]_0/[AIBN]_0$ ratio of 5/1 (Table 1), yielding polymers with low $M_w/M_n$ values (~1.2) and reasonable agreement between experimental and theoretical molecular weights. Polymers with close molecular weights were targeted in order to eliminate LCST drifts influenced by effects of polymer chain lengths.

Temperature- and pH-responsive random copolymers of N-isopropylacrylamide (NIPAAm) and propylacrylic acid (PAA) were prepared using the reversible addition fragmentation chain transfer (RAFT) polymerization method. The lower critical solution temperatures (LCSTs) (or phase separation temperatures) of the NIPAAm-co-PAA copolymer solutions were measured by the cloud point method. At slightly acidic conditions, the LCST decreased with increase in PAA content, which suggests that the hydrophobic propyl group of PAA has a greater influence on the LCST than the polar carboxylic acid group at those conditions. An increase of pH led to a significant increase in LCST of the copolymers due to the ionization of the —COOH group. Because the $pK_a$ of the polymers can be tuned to fall close to neutral pH, these polymer compositions can be designed to have phase transitions triggered near physiological pH or at slightly acidic pH values that fall within acidic gradients found in biology. The NIPAAm-co-PAA copolymers thus display tunable properties that could make them useful in a variety of molecular switching and drug delivery applications where responses to small pH changes are relevant.

Temperature- and pH-Responsive Hydrogels. In another aspect, the polymer composition of the invention is a hydrogel having both pH- and temperature-responsiveness. The hydrogels of the invention are derived from copolymerization of a pH-responsive monomer and a temperature-responsive monomer. The pH-responsive monomer imparts reversible transitions between hydrophilic and hydrophobic states to the hydrogel and the temperature-responsive monomer imparts reversible transitions between expanded and contracted states to the hydrogel.

In another aspect of the invention, a temperature- and pH-responsive hydrogel is provided. In one embodiment, the hydrogel comprises a crosslinked copolymer, wherein the copolymer comprises:
 (a) temperature-responsive repeating units, wherein the repeating unit is an N-alkylacrylamide repeating unit; and
 (b) pH-responsive repeating units, wherein the repeating unit a C2-C8 alkylacrylic acid repeating unit.

In one embodiment, the hydrogel exhibits a phase transition at a pH of from about pH 5.0 to about pH 7.4.

In one embodiment, the N-alkylacrylamide is a C3-C8 alkyl N-alkylacrylamide. In one embodiment, the N-alkylacrylamide is N-isopropylacrylamide.

In one embodiment, the C2-C8 alkylacrylic acid is a C2-C8 n-alkylacrylic acid. In one embodiment, the C2-C8 alkylacrylic acid is selected from the group consisting of ethylacrylic acid, n-propylacrylic acid, and n-butylacrylic acid. In one embodiment, the C2-C8 alkylacrylic acid is n-propylacrylic acid.

In one embodiment, the N-alkylacrylamide is N-isopropylacrylamide and the C2-C8 alkylacrylic acid is propylacrylic acid.

In one embodiment, the pH-responsive repeating units are present in the copolymer in an amount from about 1 to about 50 weight percent.

In one embodiment, the hydrogel further comprises one or more therapeutic drugs or diagnostic agents. In one embodiment, the therapeutic drug or diagnostic agent is selected from the group consisting of a protein, a peptide, and a nucleic acid.

In one embodiment, the hydrogel further comprises a sugar. In one embodiment, the sugar is trehalose.

Hydrogels made from the polyacrylic acid (PAA)/polypropylacrylic acid (PPAA) polymer compositions exhibit a surprisingly sharp phase transition that can be driven by pH alterations around neutral conditions, or by small temperature changes around neutral pH. These properties are distinctly different from those polymer compositions with other pH/temperature sensitive hydrogels, such as N-isopropylacrylamide-co-acrylic acid (NIPAAm-co-AA) copolymer hydrogels. The phase transition behavior for NIPAAm-co-PAA copolymer hydrogels, representative hydrogels of the invention, are mainly due to the relatively high $pK_a$ of PPAA. At slightly acidic condition, PAA units in the hydrogel networks are hydrophobic, and the cooperatively hydrophobic interaction of pNIPAAm is thus retained or even enhanced, leading to the sharp phase-transition behavior and a decrease in the temperature at which the phase transition is induced. In addition, rapidly responsive NIPAAm-co-PAA copolymer hydrogels can be made using PEG as a pore-forming agent during polymerization. Representative dual pH/temperature sensitive NIPAAm-co-PAA copolymer hydrogels of the invention find applications where sharp responses under mild pH conditions are required.

Figure 6:
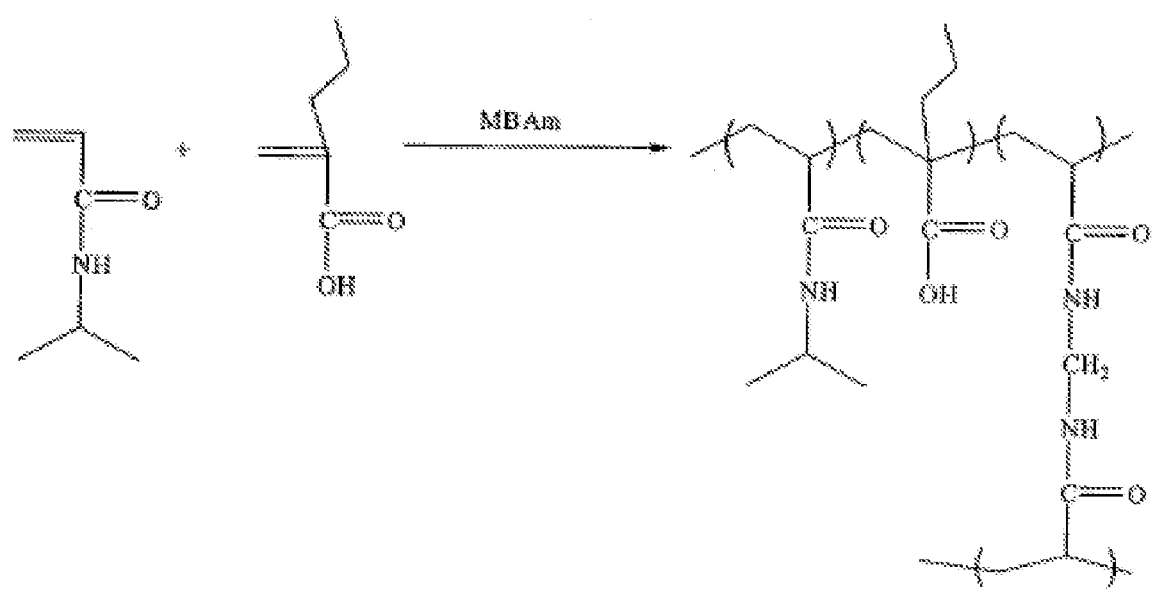
FIG. 6 is a schematic illustration of the free radical crosslinking copolymerization synthesis of representative NIPAAm-co-PAA copolymer hydrogels of the invention.

The preparation and characterization of representative hydrogels of the invention, dual pH/temperature sensitive NIPAAm-co-PAA copolymer hydrogels, is described in Example 2. The preparation of the representative hydrogels is illustrated schematically in FIG. 6.

The representative hydrogels were prepared by free-radical crosslinking copolymerization of NIPAAm and propylacrylic acid with N,N'-methylenebisacrylamide (crosslinker) in water using ammonium persulfate as initiator and N,N,N'N'-tetramethylethylenediamine as accelerator. The phase transition temperature of the hydrogel was defined as the temperature where the equilibrium swelling ratio decreases to half of the full swelling.

Figure 7A:
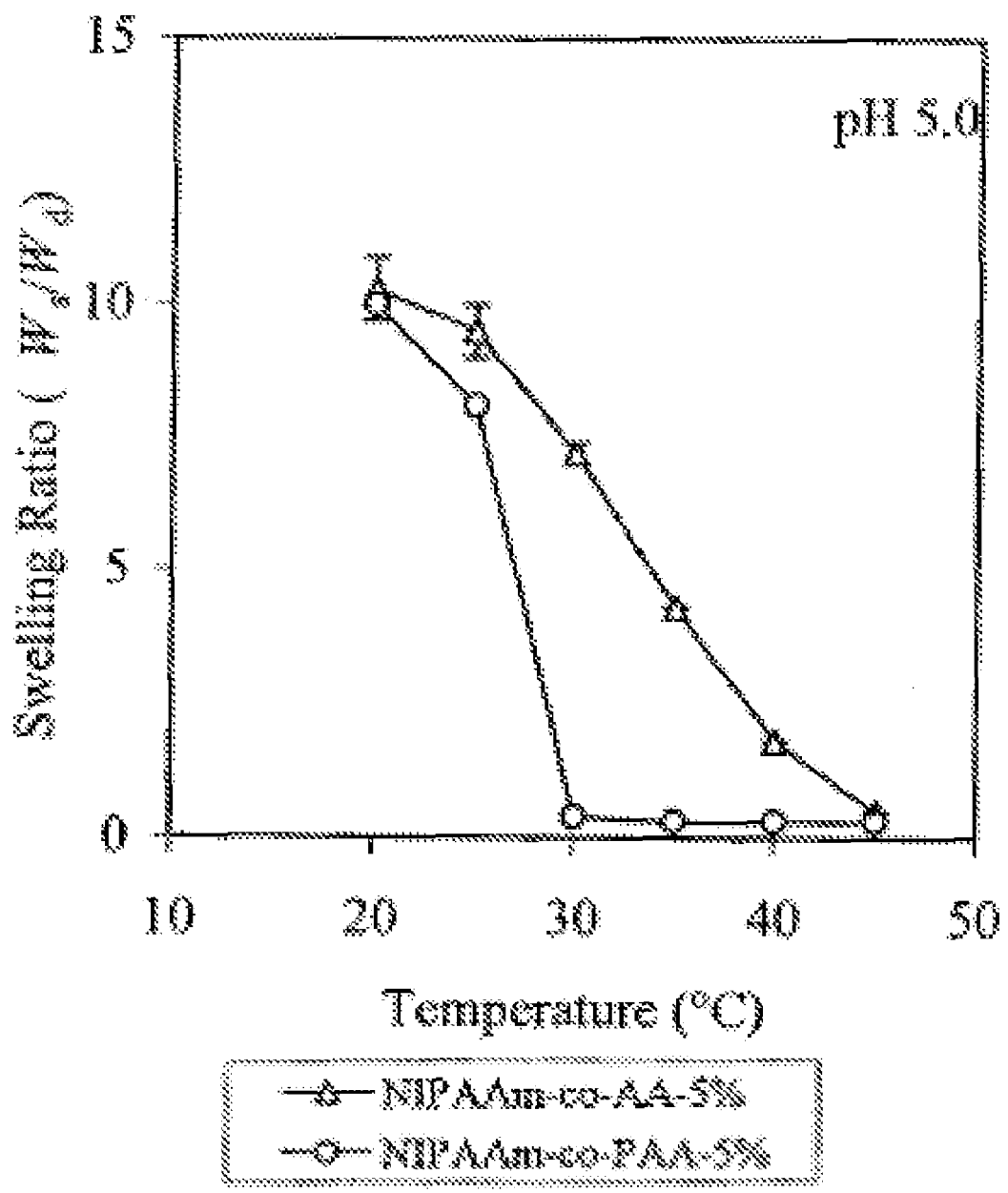
FIGS. 7A-7C are graphs comparing equilibrium swelling ratios for hydrogels of N-isopropylacrylamide-co-acrylic acid (NIPAAm-co-AA-5%) and N-isopropylacrylamide-co-propylacrylic acid (NIPAAm-co-PAA-5%) with 5 mol acid comonomer units as a function of temperature at pH 5.0, 6.5, and 7.4, respectively (measurements in triplicate)
Figure 7B:
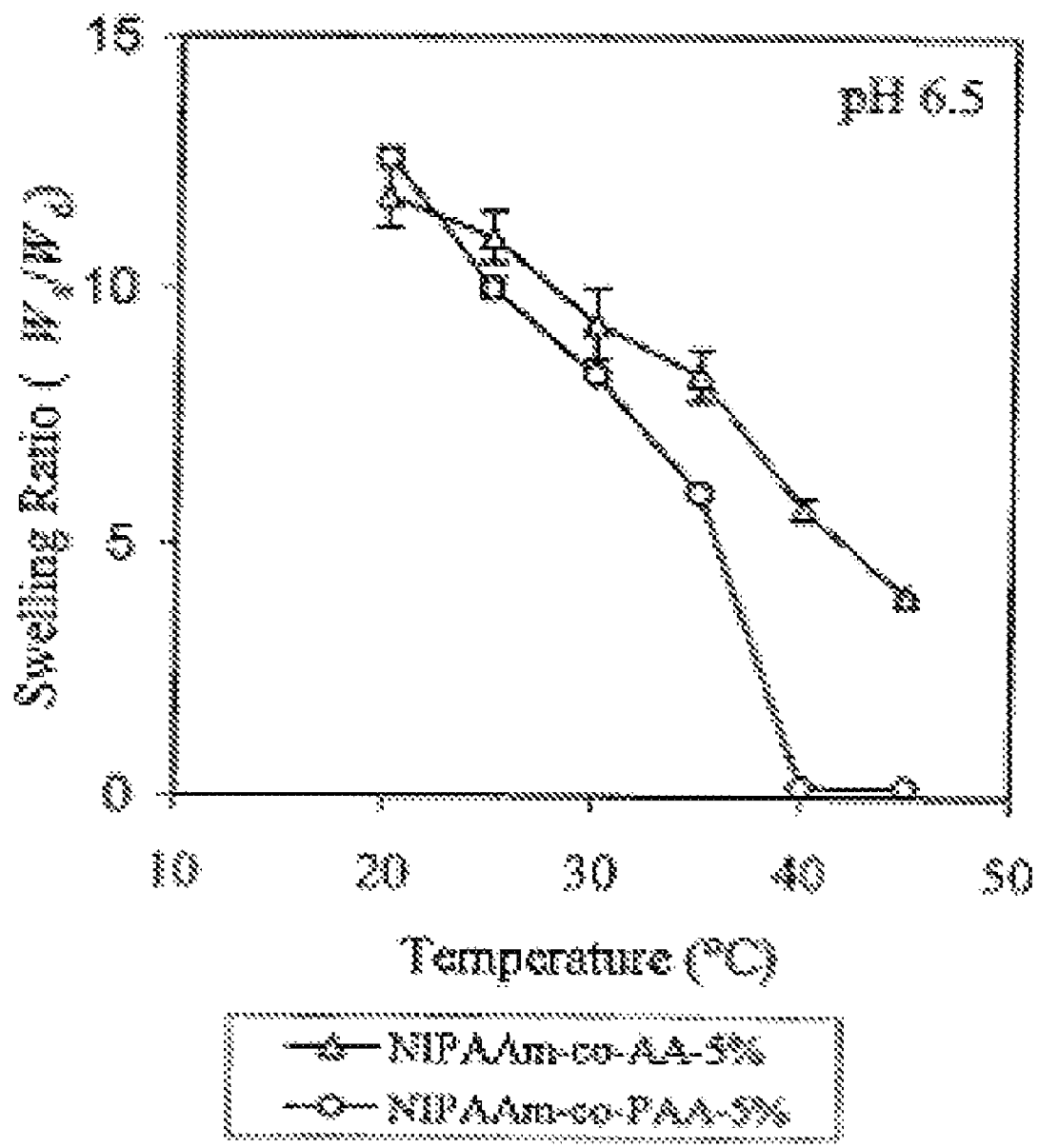
Figure 7C:
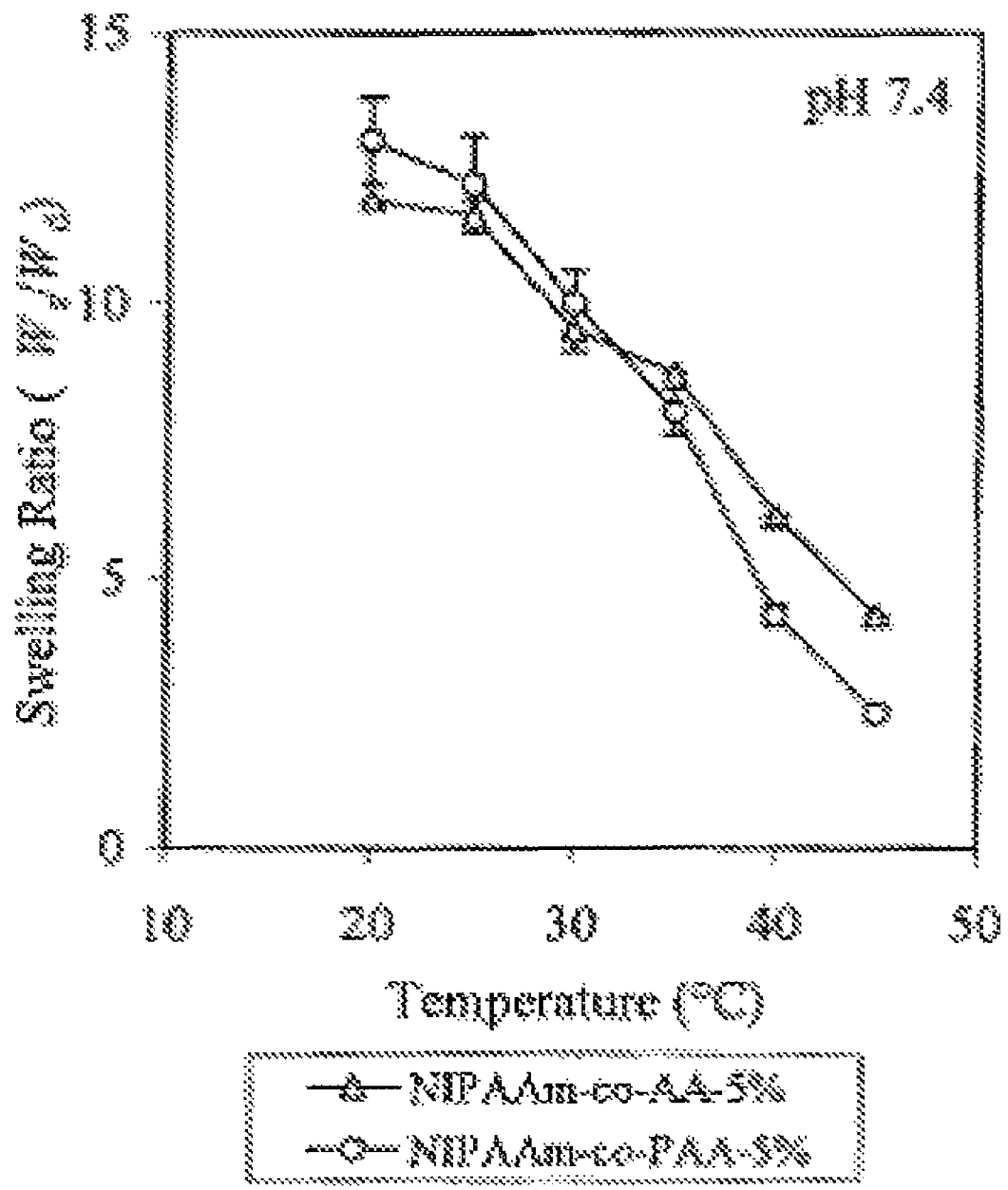

The temperature- and pH-dependent equilibrium swelling behaviors of N-isopropylacrylamide-co-propylacrylic acid (NIPAAm-co-PAA) hydrogel and N-isopropylacrylamide-co-acrylic acid (NIPAAm-co-AA) hydrogel are compared in FIGS. 7A-7C. N-Isopropylacrylamide-co-acrylic acid (NIPAAm-co-AA) hydrogel was prepared as described for N-isopropylacrylamide-co-propylacrylic acid (NIPAAm-co-PAA) hydrogel in Example 2 except acrylic acid was used rather than propylacrylic acid. In FIGS. 7A-7C compare the thermo-responsive behaviors of two NIPAAm copolymer hydrogels with 5 mol % propylacrylic acid (NIPAAM-co-PAA-5%) or acrylic acid (NIPAAM-co-AA-5%) comonomer unit at pH 5.0, 6.5 and 7.4, respectively. NIPAAM-co-PAA- 5% hydrogel shows an abrupt phase transition at temperature of about 26° C. at pH 5.0. However, no abrupt phase transition was observed for NIPAAM-co-AA-5% hydrogel. Instead, the phase transition became continuous upon raising temperature. Such significantly different thermo-responsive behaviors of NIPAAM-co-PAA and NIPAAM-co-AA hydrogels are mainly due to the pKa of acid units in the gel network. Poly(acrylic acid) ($pK_a \approx 4.25$) has a much lower $pK_a$ than poly(propylacrylic acid) ($pK_a > 6.0$). At pH 5.0, most of acrylic acid units of NIPAAM-co-AA hydrogel become charged and more polar, which will increase or eliminate the LCST of pNIPAAm copolymers. In addition, the copolymer chains will also expand due to the electrostatic repulsion between charged sites along the backbone and osmotic pressure resulting from counterion ingress. Together, these effects will restrict the temperature-induced hydrophobic aggregation, leading to decreased or no thermo-responsive properties of NIPAAM-co-AA gels. However, as for NIPAAm-co-PAA hydrogel, propylacrylic acid is in the acidic form and is hydrophobic at pH 5.0. The cooperatively hydrophobic interaction of pNIPAAm is thus retained or enhanced, leading to the sharp temperature-induced phase transition and a decrease in the LCST of NIPAAm-co-PAA hydrogel. The hydrophobic interactions turn to be dominant and the polymer chains aggregate and dehydrate abruptly at temperature above the LCST.

Referring to FIG. 7B, at pH 6.5, few propylacrylic acid units in NIPAAm-co-PAA-5% hydrogel are dissociated and become polar, the phase transition temperature is increased and broaden (see FIG. 7A), but the hydrogel still shows abrupt phase transition at a temperature about 35° C. Referring to FIG. 7C, at pH 7.4, most of propylacrylic acid units are charged, the thermo-sensitivity of NIPAAm-co-PAA hydrogel becomes significantly less and behaves very similarly as NIPAAm-co-AA hydrogel, no abrupt phase transition takes place.

Figure 8A:
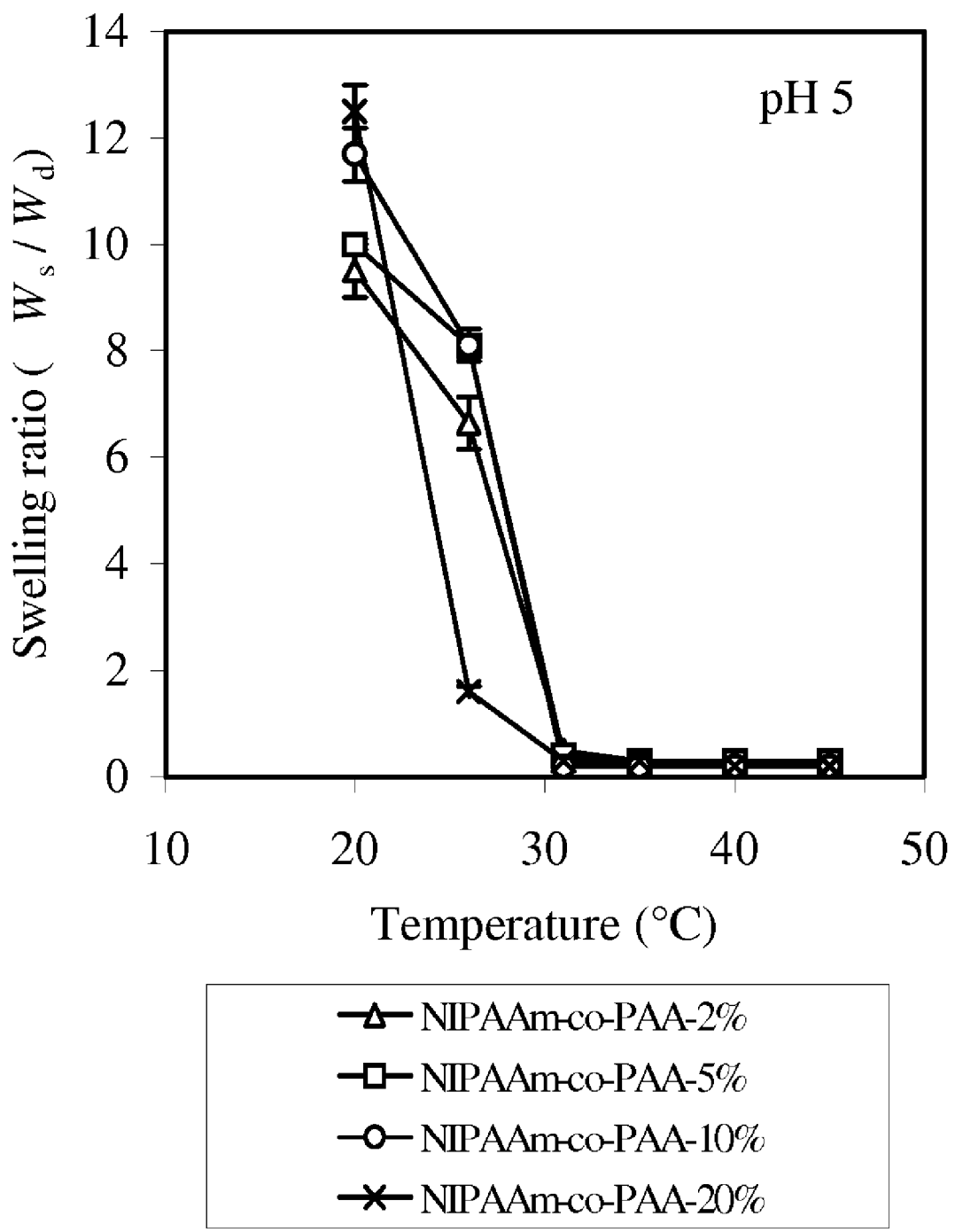
FIGS. 8A-8C are graphs illustrating equilibrium swelling curves for representative NIPAAm-co-PAA hydrogels of the invention having 2 (NIPAAm-co-PAA-2%), 5 (NIPAAm-co-PAA-5%), 10 (NIPAAm-co-PAA-10%), and 20 (NIPAAm-co-PAA-20%) mol propylacrylic acid content as a function of temperature at pH 5.0, 6.5, and 7.4, respectively (measurements in triplicate)
Figure 8B:
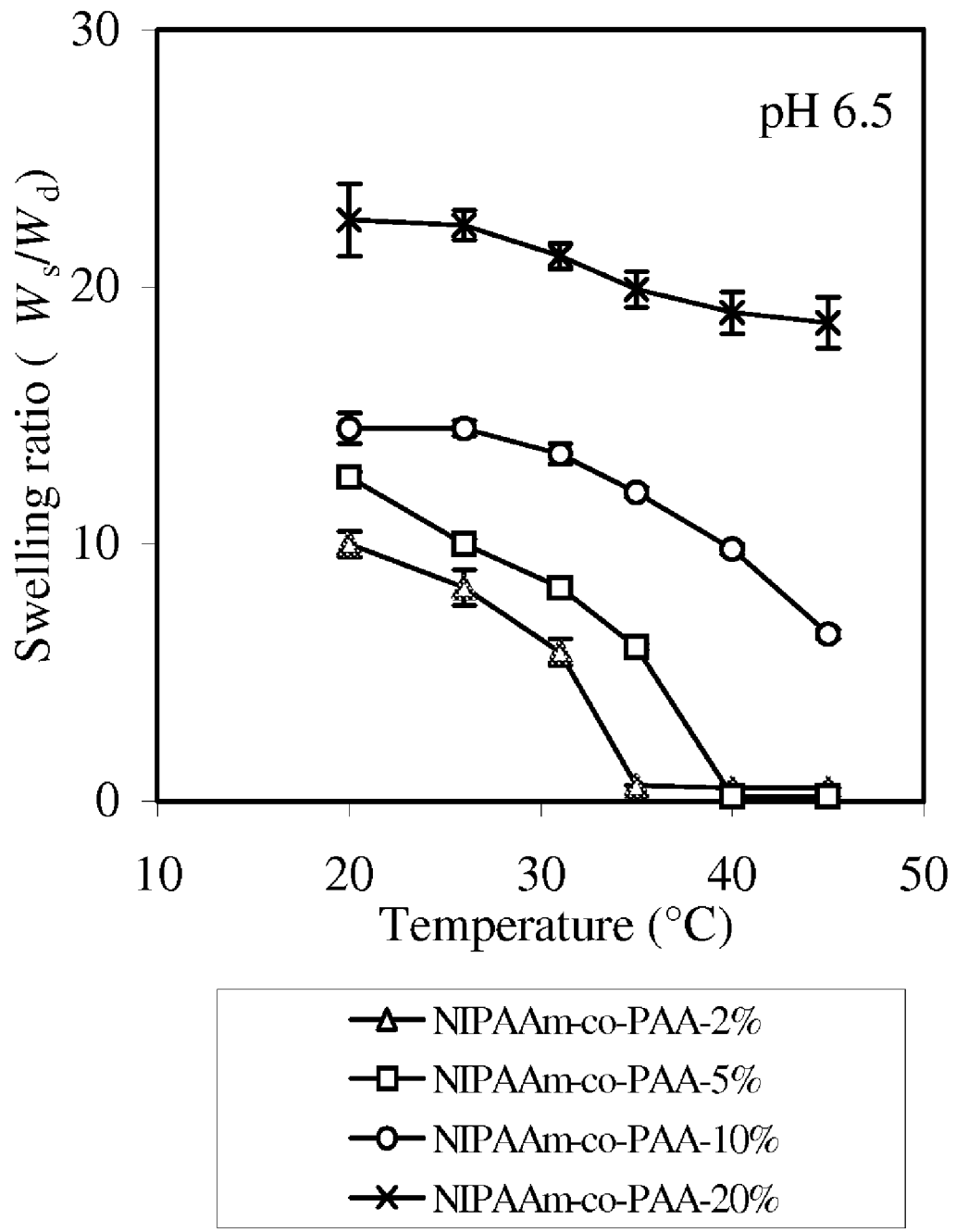
Figure 8C:
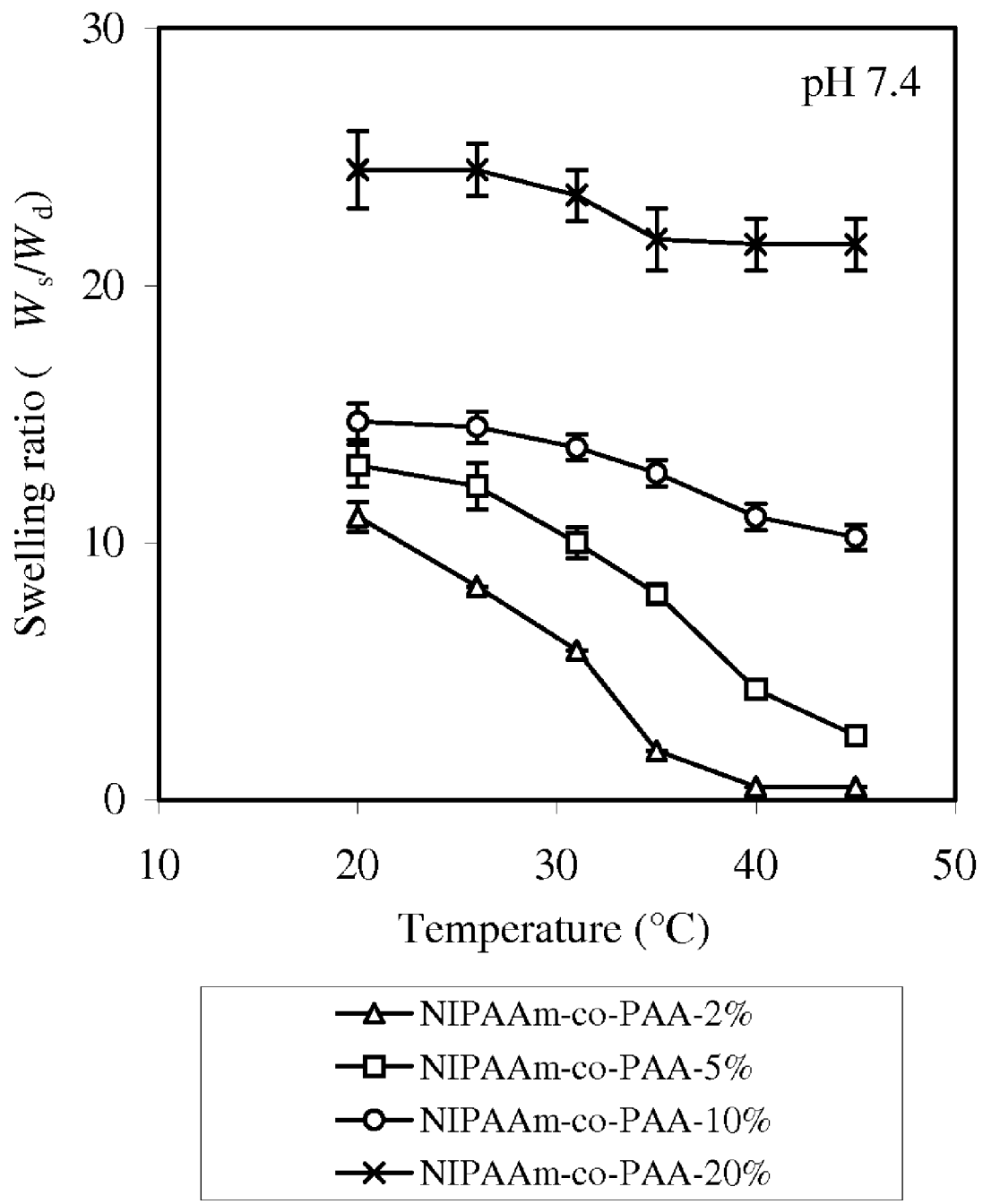

The effect of PAA content in the representative NIPAAm-co-PAA hydrogels of the invention on their combined pH- and temperature-responsive behavior is illustrated in FIGS. 8A-8C. FIGS. 8A-8C illustrate the equilibrium swelling curves for a series of NIPAAm-co-PAA hydrogels having 2 (NIPAAm-co-PAA-2%), 5 (NIPAAm-co-PAA-5%), 10 (NIPAAm-co-PAA-10%), and 20 (NIPAAm-co-PAA-20%) mol propylacrylic acid content as a function of temperature at pH 5.0, 6.5 and 7.4, respectively. As discussed above, propylacrylic acid is in the acidic form and is hydrophobic at pH 5.0. Referring to FIG. 8A, each of the NIPAAm-co-PAA hydrogels are temperature-responsive and show sharp phase transition, and the phase transition temperatures decrease with increasing propylacrylic acid content in the hydrogel. The hydrogel with 20 mol % propylacrylic acid content has phase transition at about 22° C. Referring to FIG. 8A, at pH 6.5, the NIPAAm-co-PAA hydrogels with low propylacrylic acid contents (2 and 5 mol %) show abrupt phase transition upon increasing temperature. However, the thermo-sensitivity of the hydrogels with high propylacrylic acid content (10 and 20 mol %) is significantly less, no abrupt phase transition is observed. NIPAAm-co-PAA-20% is almost not thermoresponsive, indicating that both the percentage of PAA and the pH are important to the thermo-responsive properties of NIPAAm-co-PAA hydrogels. As the pH is increased, the swelling ratio of NIPAAm-co-PAA-20% hydrogel is much higher than those of NIPAAm-co-PAA hydrogels with lower acid unit contents due to the high content of ionized groups. Upon reaching a certain content, the ionized propylacrylic acid units significantly reduce the effect of any hydrophobically bound water, and convey sufficient solubility to offset the hydrophobic temperature-sensitive NIPAAm components. In addition, the ionized sites of hydrogel could increase polymer chain hydration due to both an increases osmotic pressure resulting from counterion ingress and chain-chain Coulombic repulsion, thereby inhibiting the hydrogel collapse upon raising temperature.

Referring to FIG. 8C, at pH 7.4, a majority of the propylacrylic acid is ionized, the thermo-sensitivity of hydrogels is significantly reduced by a further increase in hydrophilicity of polymer chains, osmotic pressure and Coulombic repulsion.

For applications in delivering reagents for diagnostic applications and in drug delivery, the response rates of these hydrogels are also important. The rate of hydrogel response is known to be controlled by diffusion of water into or out of the polymeric hydrogel matrix, and the diffusion of polymer networks toward the surrounding water. Thus, the response rate can be improved by reducing the hydrogel dimension, hydrogels in micro- or nano-size respond rapidly. Faster swelling response of hydrogels can also be achieved by changing the gel structure or the gel morphology to a porous inhomogeneous network structure. The use of pore-forming agents friendly to bioproducts, such as sugar and polyethylene glycol (PEG), are attractive and simple approaches.

In one embodiment, the hydrogels of the invention were prepared using polyethylene glycol and have more porous morphologies. Representative NIPAAm-co-PAA hydrogels made using PEG provided hydrogels having relatively porous inhomogeneous structures compared to those hydrogels prepared without the use of PEG.

Figure 9:
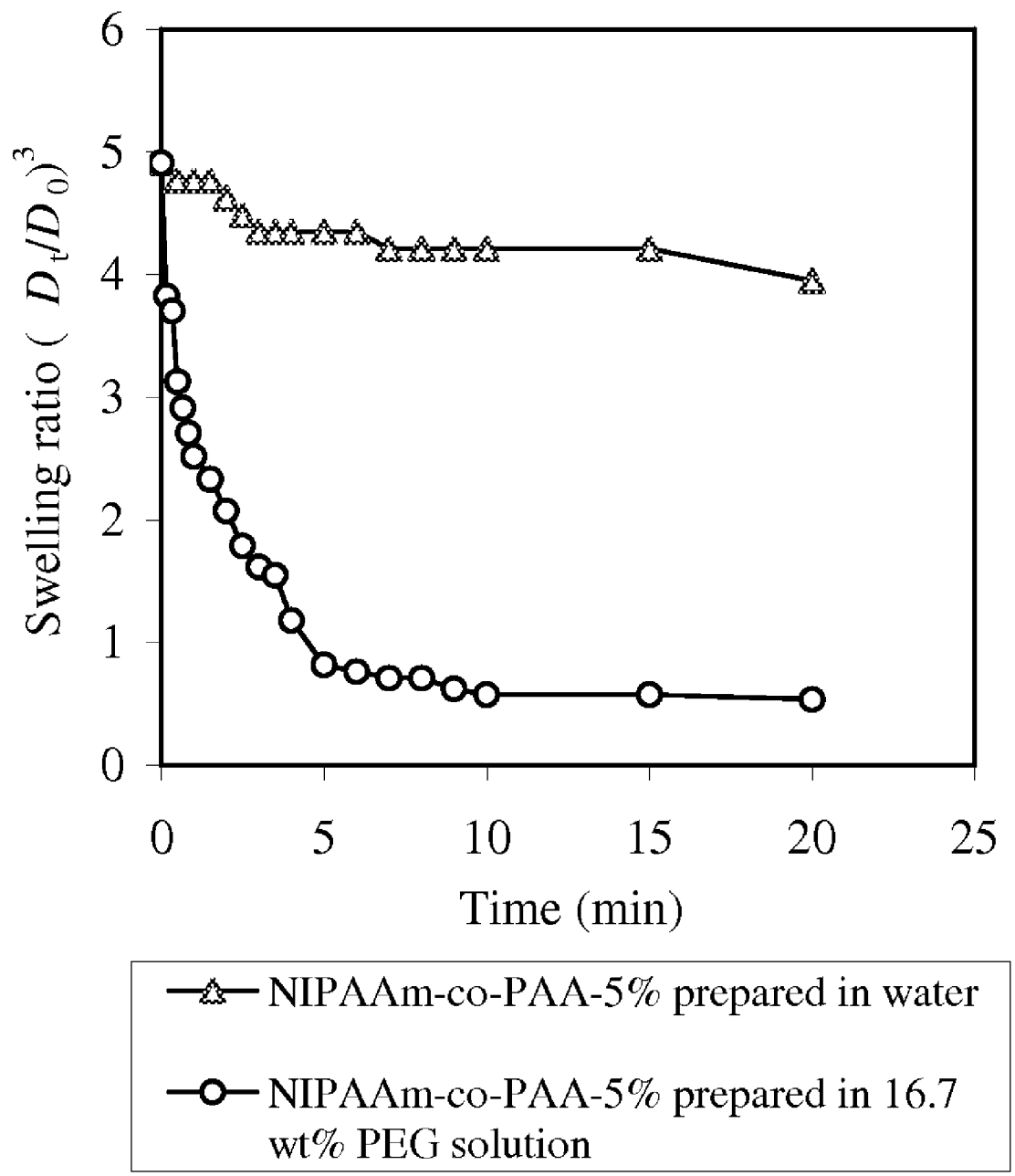
FIG. 9 is a graph comparing the time dependency of the deswelling ratio $(D_t/D_0)^3$ for two representative NIPAAm-co-PAA-5% hydrogels of the invention upon temperature change from room temperature (20° C.) to 35° C. at pH 5.0: the first NIPAAm-co-PAA-5% hydrogel was prepared in water (Δ); the second NIPAAm-co-PAA-5% hydrogel (○) was prepared in 16.7 weight percent polyethylene glycol (PEG) having molecular weight 2000.

To observe hydrogel response behavior in real time, the diameter change of hydrogels was measured using an optic microscope. FIG. 9 is a graph comparing the time dependency of the deswelling ratio $(D_t/D_0)^3$ for two representative NIPAAm-co-PAA-5% hydrogels of the invention upon temperature change from room temperature (20° C.) to 35° C. at pH 5.0: the first NIPAAm-co-PAA-5% hydrogel was prepared in water (Δ); the second NIPAAm-co-PAA-5% hydrogel (○) was prepared in 16.7 weight percent polyethylene glycol (PEG) having molecular weight 2000. The second hydrogel having a porous morphology. In the measurement, the hydrogels were rapidly transferred from phosphate buffer (PB) buffer of 20° C. to warmer PB buffer of 35° C. The volume transition NIPAAm-co-PAA-5% hydrogel is only about 10% after 20 min compared to the final equilibrium deswelling state. However, the response rate of NIPAAm-co-PAA-5% hydrogel prepared in PEG solution is significantly more rapid, as it loss most of its water within 2 min and reaches the final equilibrium state in less than 5 min. In the presence of PEG, the hydrogel polymer network is in expanded conformation that creates a porous structure that allows faster water exchange.

Figure 18:
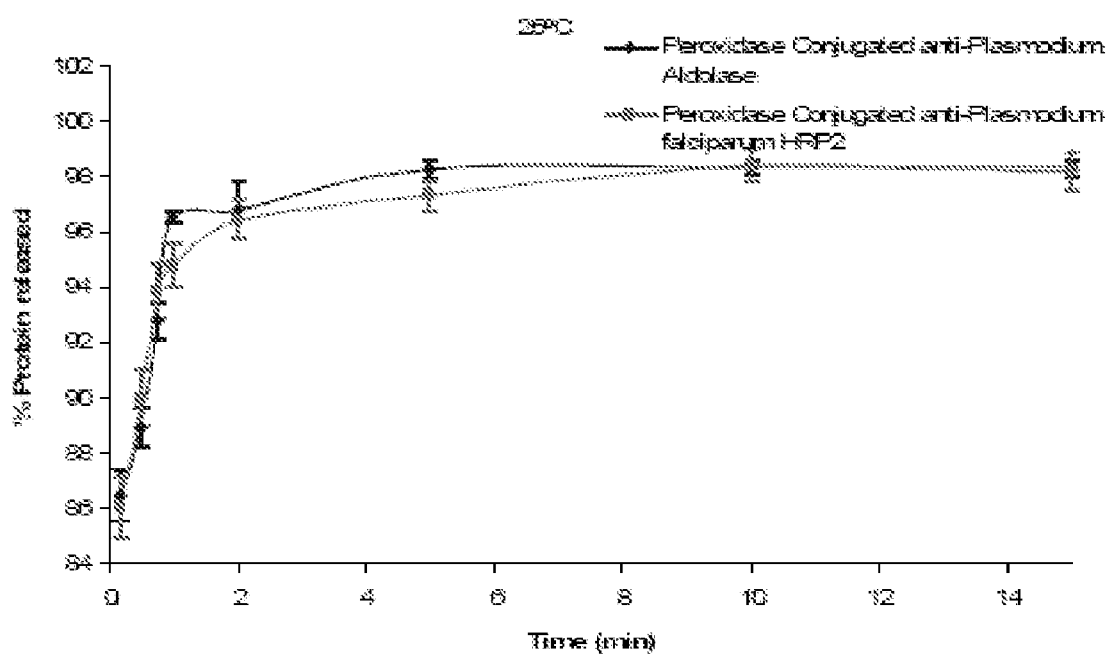
FIG. 18 is a graph illustrating protein release from membrane-bound pNIPAAm-co-PAA hydrogels of the invention over time (release within 4 min at 25° C.)
Figure 19:
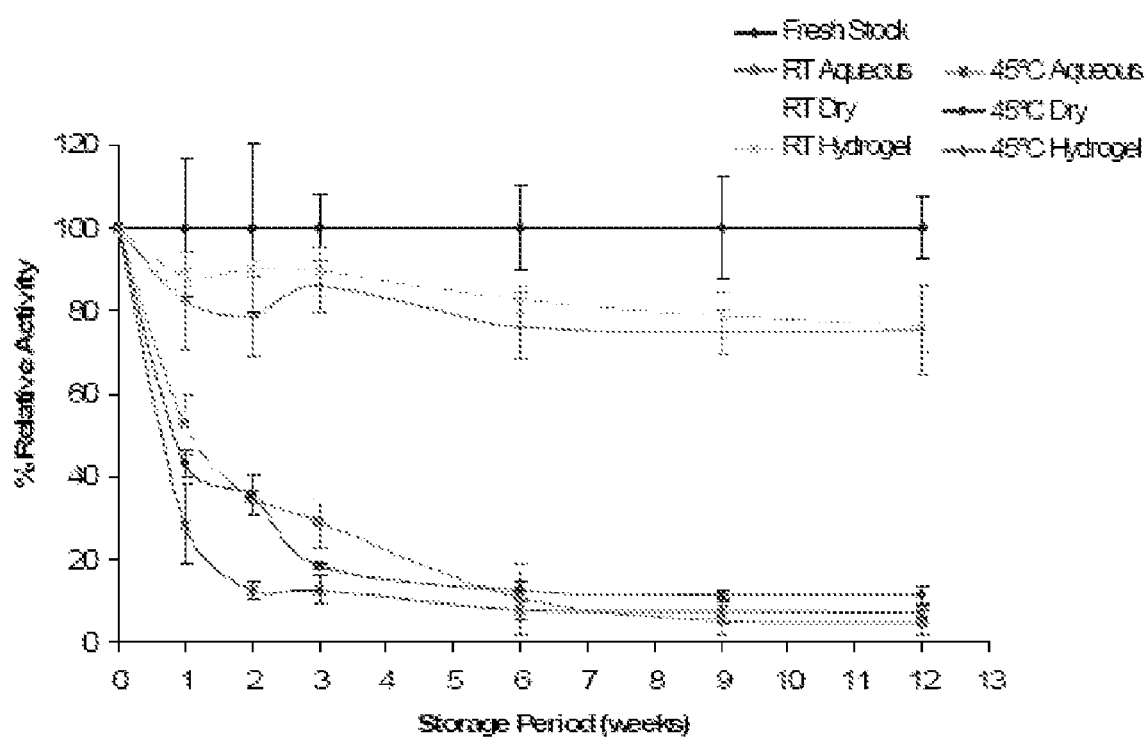
FIG. 19 is a graph comparing relative activity of stored protein versus storage period (12 weeks) at 4° C. for representative hydrogels of the invention and stock solutions.

The preparation of representative hydrogels of the invention and their use to store and release therapeutic drugs or diagnostic agents is described in Example 3. FIG. 18 is a graph illustrating protein release from membrane-bound pNIPAAm-co-PAA hydrogels of the invention over time (release occurred within 4 min at 25° C.). FIG. 19 is a graph comparing relative activity of stored protein versus storage period (12 weeks) at 4° C. for representative hydrogels of the invention and stock solutions.

In another embodiment, the hydrogels of the invention were prepared incorporating sugars into the hydrogels. Stimuli-responsive hydrogels useful for storage and delivery of proteins, such as antibodies for diagnostic assays, can be enhanced through the covalent incorporation of stable sugars often used in protein preservation. Such sugars, such as the disaccharide trehalose, are known to stabilize proteins exposed to extremes in temperature and pH as well as low moisture conditions. Modification of these sugars with reactive groups frequently used in polymerization, such as acrylates and methacrylates, can provide copolymer hydrogel formulations capable of the long-term storage of proteins in suboptimal conditions without loss of protein function. This embodiment provides an alternative to current systems utilizing sugars for protein preservation in which the sugar is delivered with the protein, thus contaminating the sample. Grafted or crosslinked sugar hydrogels provide a matrix in which proteins can be preserved and released upon exposure to the proper stimuli, while retaining the preservative and delivering a pure sample.

Thus, in one aspect, the invention provides dual pH- and temperature-sensitive hydrogels based on dual pH- and temperature-sensitive copolymers (e.g., N-isopropylacrylamide-co-propylacrylic acid (NIPAAm-co-PAA) copolymers) prepared by free radical polymerization. In contrast to N-isopropylacrylamide-co-acrylic acid copolymer hydrogels, the NIPAAm-co-PAA copolymer hydrogels exhibit temperature-induced sharp phase transition at pH close to neutral conditions due to the high pKa of polypropylacrylic acid. At slightly acidic condition, propylacrylic acid units in the hydrogel networks are hydrophobic, thus the cooperatively hydrophobic interaction of pNIPAAm is retained or even enhanced, leading to the sharp phase transition and a decrease in the LCST of NIPAAm-co-PAA hydrogel. At both low and high PAA contents, a small increase in pH can cause dramatic increases in the LCST. Thus, the LCST can be adjusted to any desired range at a particular pH value. The response rate of NIPAAm-co-PAA copolymer hydrogel is improved significantly using PEG as a pore-forming agent during polymerization. Such rapid responsive hydrogels find utility in microactuators and drug delivery devices where sharp responses under mild pH changes are required.

Temperature- and pH-Responsive Block Copolymers. In another aspect, the polymer composition of the invention is a block copolymer having both pH- and temperature-responsiveness. The block copolymers include a random copolymer of the invention having both pH- and temperature-responsiveness, as described above, coupled to a hydrophobic block.

In another aspect, the present invention provides a temperature- and pH-responsive block copolymer. In one embodiment, the block copolymer, comprises:
(a) a first block comprising a random copolymer comprising:
  (i) temperature-responsive repeating units, wherein the repeating unit is an N-alkylacrylamide repeating unit; and
  (ii) pH-responsive repeating units, wherein the repeating unit a C2-C8 alkylacrylic acid repeating unit; and
(b) a second hydrophobic block.

In one embodiment, the copolymer exhibits a phase transition at a pH of from about pH 5.0 to about pH 7.4.

In one embodiment, the N-alkylacrylamide is a C3-C8 alkyl N-alkylacrylamide. In one embodiment, the N-alkylacrylamide is N-isopropylacrylamide.

In one embodiment, the C2-C8 alkylacrylic acid is a C2-C8 n-alkylacrylic acid. In one embodiment, the C2-C8 alkylacrylic acid is selected from the group consisting of ethylacrylic acid, n-propylacrylic acid, and n-butylacrylic acid. In one embodiment, the C2-C8 alkylacrylic acid is n-propylacrylic acid.

In one embodiment, the N-alkylacrylamide is N-isopropylacrylamide and the C2-C8 alkylacrylic acid is propylacrylic acid.

In one embodiment, the pH-responsive repeating units are present in the random copolymer in an amount from about 1 to about 20 weight percent. In one embodiment, the random copolymer has a molecular weight of from about 5,000 to about 20,000.

In one embodiment, the block copolymer has a molecular weight of from about 15,000 to about 60,000.

In one embodiment, the hydrophobic block is selected from the group consisting of a polystyrene, a poly(methylmethacrylate), a poly(ethylacrylate), a poly(butylacrylate), a poly(glycotide-co-lactide), and a polyoxyethylene-polyoxypropylene copolymer. In one embodiment, the hydrophobic block is selected from the group consisting of a poly(ethylacrylate) and a poly(butylacrylate).

The block copolymers are made by combining the alkyl (acrylic acids) such as PAA together with NIPAAm into a random block that can be combined with a hydrophobic block such as polystyrene, poly(methylmethacrylate), poly(ethylacrylate), poly(butylacrylate), poly(glycotide-co-lactide) (PLGA), and polyoxyethylene-polyoxypropylene copolymers (POLOXAMER and PLURONIC copolymers). The lengths can be controlled by the RAFT synthesis technique. A representative block copolymer of the invention, poly (NIPAAm-co-PAA)-poly(butylacrylate) has the following properties where n refers to the first block and m to the second block, respectively: (1) for n=38 and m=140, Mn=26,500, PDI=1.20; (2) for n=38 and m=80, Mn=20,400, PDI=1.24; (3) for n=60 and m=150, Mn=34,900, PDI=1.40; and (4) for n=60 and m 90, Mn=26,400, PDI=1.44.

Figure 10:
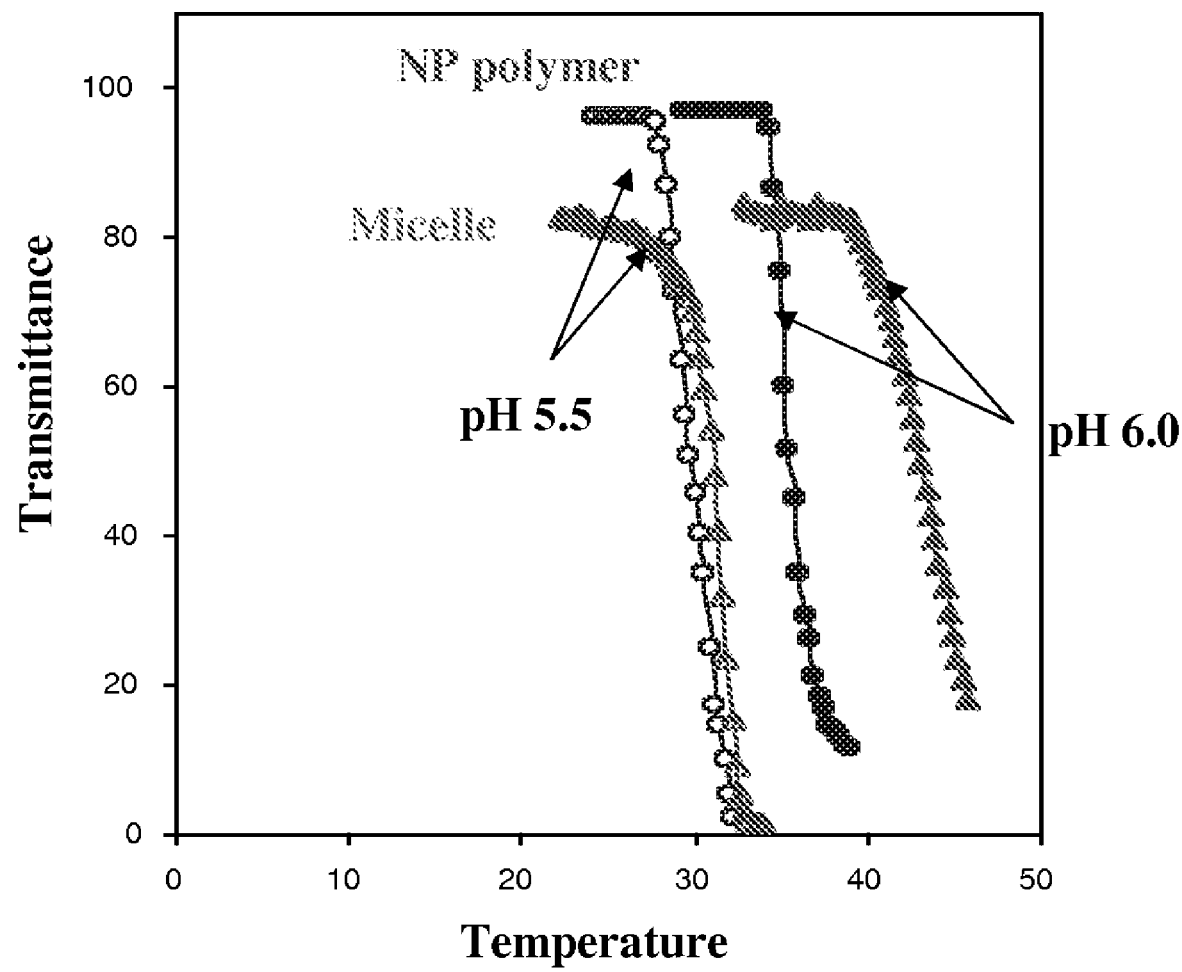
FIG. 10 illustrates the phase transitions for a representative poly(NIPAAm-co-PAA)-poly(butylacrylate) block copolymer of the invention (n=38, m=80, Mn=20,400, PDI=1.24)

FIG. 10 illustrates the phase transitions for a representative poly(NIPAAm-co-PAA)-poly(butylacrylate) block copolymer of the invention (n=38, m=80, Mn=20,400, PDI=1.24).

The block copolymers of the invention can self-assemble into micelles. The sizes of the polymeric micelles for a representative block copolymer of the invention have been determined by dynamic light scattering techniques and by transmission electron microscopy. Table 3 summarizes the sizing data for representative poly(NIPAAm-co-PAA)-poly(butylacrylate) block copolymers obtained by dynamic light scattering (DLS) characterization.

TABLE 3

Representative block copolymers' micelle size at pH 7.4

| Block Copolymer | | $D_h$ at RT | $D_h$ at 37° C. |
|---|---|---|---|
| n = 38 | m = 140 | 40 nm | 94 nm |
| n = 38 | m = 80 | 28 nm | 29 nm |
| n = 60 | m = 150 | 35 nm | 88 nm |
| n = 60 | m = 90 | 36 nm | 35 nm |

Figure 11:
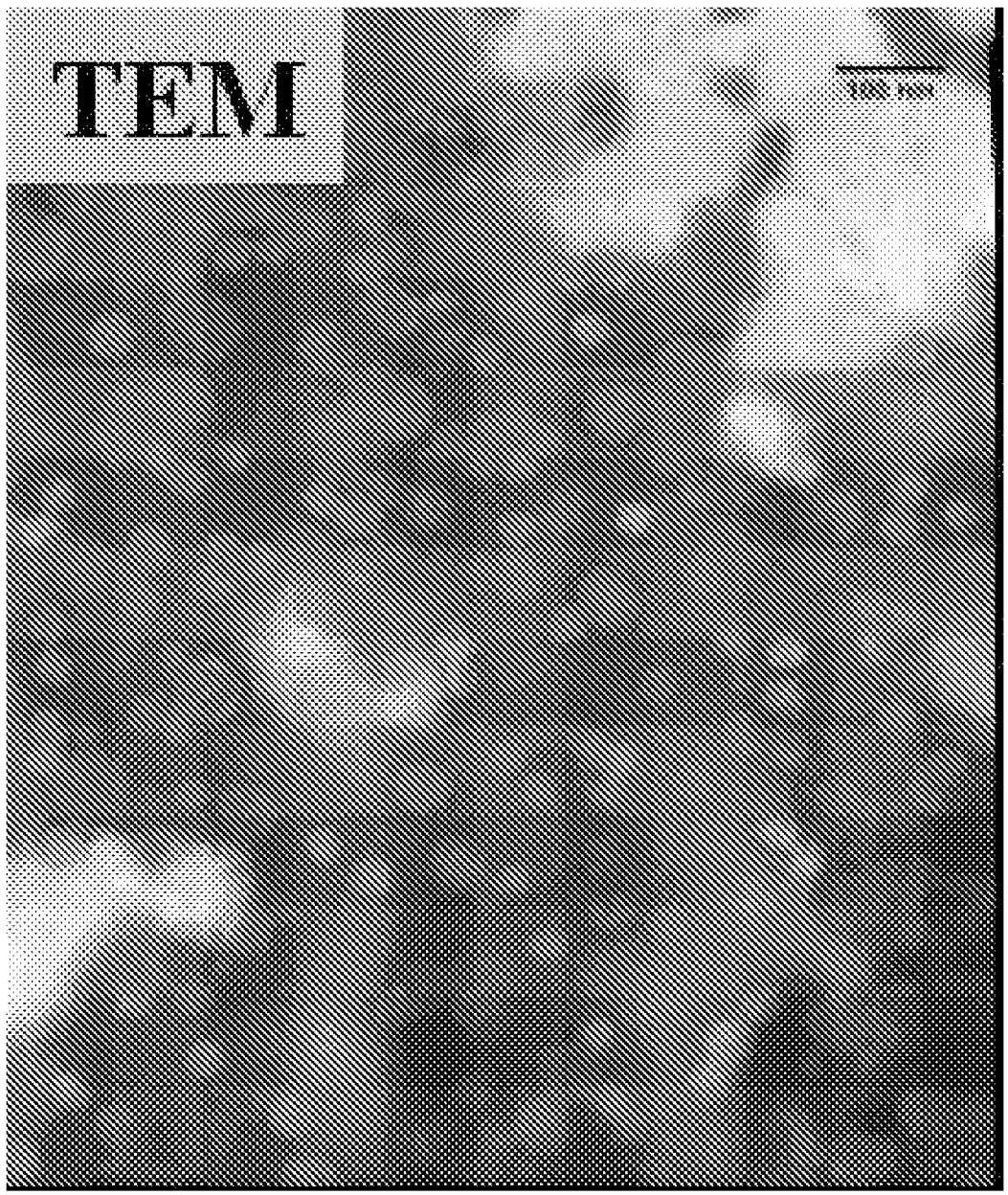
FIG. 11 is a transmission electron microscope (TEM) image of micelles formed from a representative poly(NIPAAm-co-PAA)-poly(butylacrylate) block copolymer of the invention.

FIG. 11 is a transmission electron microscope (TEM) image of micelles formed from a representative poly (NIPAAm-co-PAA)-poly(butylacrylate) block copolymer of the invention.

Diblock Copolymer Micelles. In one embodiment, the block copolymers of the invention provide temperature- and pH-responsive polymeric micelles useful for therapeutic drug or diagnostic agent delivery.

Temperature- and pH-responsive diblock copolymers were prepared by sequential monomer polymerization using the reversible addition fragmentation chain transfer (RAFT) polymerization method. A representative diblock copolymer is poly(N-isopropylacrylamide-co-propylacrylic acid)-block-poly(ethylacrylate) ((NIPAAm-co-PAA)-block-EA). These representative diblock copolymers were utilized to fabricate micelles with a hydrophilic and pH/temperature responsive shell of the NIPAAm-co-PAA copolymer and a hydrophobic gel-like core of the pEA block. The hydrodynamic diameters of the micelles at various pHs and temperatures were determined by dynamic light scattering (DLS). By tuning the compositions of block copolymers, the polymeric micelles formed were stabilized at physiological conditions (pH 7.4, 37° C.), but were shown to deform and aggregate at slightly acidic conditions (pH≧5.5) due to the phase change of the shell-forming NIPAAm-co-PAA copolymers. The sharp pH- and temperature-responsive properties of these polymeric micelles provide triggered drug delivery at therapeutic targets including tumor tissue and in acidic intracellular vesicles such as endosomes and lysosomes.

The preparation and characterization of a representative temperature and pH-responsive diblock copolymer of the invention, (NIPAAm-co-PAA)-block-EA, useful making polymeric micelles for therapeutic drug or diagnostic agent delivery is described in Example 4.

Figure 12:
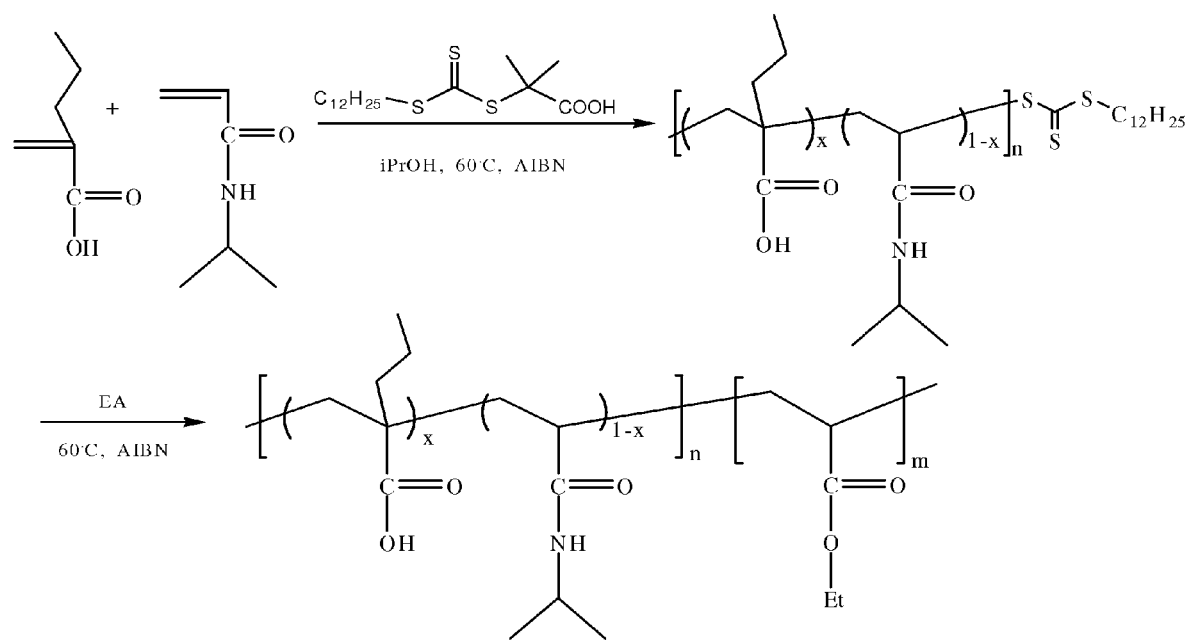
FIG. 12 is a schematic illustration of the RAFT copolymerization synthesis of representative poly(N-isopropylacrylamide-co-propylacrylic acid)-block-poly(ethyl acrylate) ((NIPAAm-co-PAA)-block-EA) block copolymers of the invention.

The synthesis of (NIPAAm-co-PAA)-block-EA block copolymers was carried out via sequential monomer polymerization using the reversible addition fragmentation chain transfer (RAFT) polymerization method. A schematic illustration of the RAFT polymerization method for making a representative block copolymer of the invention is illustrated in FIG. 12. Referring to FIG. 12, the hydrophilic block of NIPAAm-co-PAA copolymer was first synthesized by RAFT copolymerization using 2-dodecylsulfanylthiocarbonylsulfanyl-2-methyl propionic acid (DMP) as chain transfer agent (CTA) and AIBN as an initiator. The NIPAAm-co-PAA copolymers respond to the small pH changes from pH 5.5 to 7.4 at 37° C. (NIPAAm-co-PAA copolymers with less than 20 mol % PAA). The copolymers were obtained with high yield and with low $M_w/M_n$ n values via RAFT copolymerizations. The preparation details and characterization of five representative NIPAAm-co-PAA copolymers are summarized in Table 4.

Figure 13:
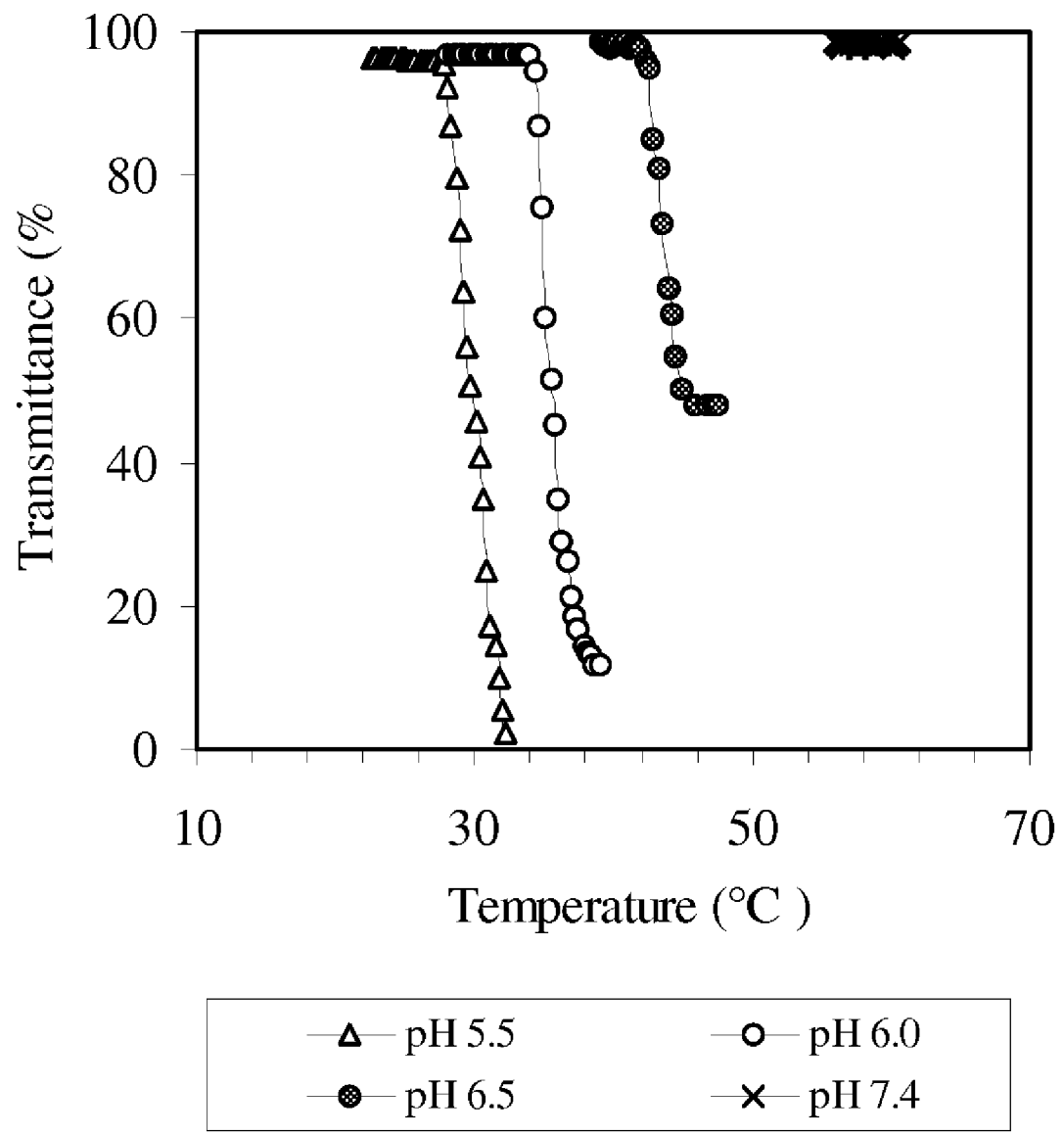
FIG. 13 is a transmission versus temperature curve comparing phase transitions for solutions of a representative NIPAAm-co-PAA copolymer (2.0 mg/ml in 0.02 mol $1^{-1}$ PB buffers (ionic strength=0.15 mol $1^{-1}$) of the invention, NIPAAm-co-PAA3, at pH 5.5, 6.0, 6.5, and 7.0.

The lower critical solution temperature (LCST) behaviors of NIPAAm-co-PAA copolymer solutions were characterized by measuring their cloud points. FIG. 13 shows typical transmittance versus temperature curves for NIPAAm-co-PAA3 at different pHs. NIPAAm-co-PAA3 solution has an LCST of around 29.8° C. at pH 5.5, 35.6° C. at pH 6.0, 42.9 at pH 6.5 and no phase transition took place at pH 7.4. The LCSTs of thermo-responsive polymers is strongly influenced by changes in the hydrophilic/hydrophobic nature of the polymer. The polar character of the PAA units changes from hydrophobic when it is protonated at slightly acidic conditions, lowering the LCST, and to highly hydrophilic upon ionization, leading to an increase in LCST. The pH dependence of LCSTs for NIPAAm-co-PAA copolymers with various PAA contents is presented in FIG. 14. The LCST varies more with pH changes for polymers having higher PAA contents. For example, NIPAAm-co-PAA1 contains only 1.5 mol % PAA, and has an LCST of 34.3° C. at pH 5.5 and 36.5° C. at pH 6.5. In contrast, NIPAAm-co-PAA5 contains 13.2 mol % PAA, and has LCSTs of 29.2° C. at pH 5.5 and 46.5° C. at pH 6.5.

An ideal NIPAAm-co-PAA copolymer to construct the block copolymers is to have an LCST above 37° C. at pH 7.4, but below 37° C. at slightly pH conditions. Thus, a slight pH change could induce a phase transition of constructed polymers and the subsequent deformation and aggregation of the formed micelles, following by the trigger release of encapsulated drug molecules. Therefore, NIPAAm-co-PAA-3, 4, and 5 were chosen as the macro-CTA for the RAFT polymerization of ethyl acrylate (EA) to form (NIPAAm-co-PAA)-block-EA block copolymers (see FIG. 12). Five representative (NIPAAm-co-PAA)-block-EA block copolymers were prepared and their characteristics are presented in Table 5. Polyethylacrylate (pEA) segments with various chain lengths in the diblock copolymers were obtained by varying the molar ratios of monomers to macro-CTA and AIBN initiator. The formation of the diblock copolymers was then confirmed by GPC and NMR measurements. As indicated in Table 5, a significant increase in molecule weight was observed after the RAFT polymerization of EA as compared to the corresponding NIPAAm-co-PAA macro-CTA. The resulting diblock copolymers had relatively narrow molecular weight distributions ($M_w/M_n$=1.2-1.4). $^1$H-NMR spectra of the diblock copolymers reveal NIPAAm unit isopropyl C—H signal at 3.9 ppm, and the ethoxy signal of pEA segments at 4.1 ppm (O—CH$_2$—).

TABLE 4

Preparation of N-isopropylacrylamide-co-propylacrylic acid (NIPAAm-co-PAA) copolymers using RAFT copolymerization.[a]

| Polymer | PAA Amount (mol %) in feed | PAA Amount (mol %) in polymer[b] | [monomer]$_0$ [CTA]$_0$ + 2[AIBN]$_0$ | Yield (wt %) | $M_n$[c] (theor) | $M_n$[d] (expt) | $M_w/M_n$ |
|---|---|---|---|---|---|---|---|
| NIPAAm-co-PAA1 | 1.0 | 1.5 | 50 | 84.6 | 4,800 | 7,500 | 1.07 |
| NIPAAm-co-PAA2 | 1.0 | 1.2 | 100 | 95.0 | 10,700 | 12,700 | 1.11 |
| NIPAAm-co-PAA3 | 5.0 | 8.5 | 50 | 80.0 | 4,500 | 7,200 | 1.11 |
| NIPAAm-co-PAA4 | 5.0 | 8.8 | 100 | 79.0 | 10,500 | 11,800 | 1.22 |
| NIPAAm-co-PAA5 | 10.0 | 13.2 | 50 | 94.0 | 5,300 | 7,600 | 1.20 |

[a]Polymerization was carried out at 60° C. for 17 h at 50 wt/v % monomer in isopropanol, 2,2'-Azobis(isobutyronitrile) (AIBN) as initiator and 2-dodecylsulfanylthiocarbonylsulfanyl-2-methyl propionic acid as chain transfer agent (CTA). [CTA]$_0$/[AIBN]$_0$ = 20.
[b]Estimated from potential titration.
[c]Mn (theor) = conversion × MW$_{monomer}$ × [M]$_0$/([CTA] + 2[AIBN]).
[d]Determined by GPC in DMF containing 0.01 mol L$^{-1}$ LiCl at 60° C. (poly(methyl methacrylate) standard).

TABLE 5

Preparation of poly(N-isopropylacrylamide-co-propylacrylic acid)-block-poly(Ethyl acrylate) ((NIPAAm-co-PAA)-block-EA) using RAFT copolymerization.[a]

| Block copolymer | Macro-CTA | EA mol %[b] | $M_n$ | $M_w/M_n$ |
|---|---|---|---|---|
| (NIPAAm-co-PAA)-block-EA-1 | NIPAAm-co-PAA3 | 79.0 | 26,500 | 1.20 |
| (NIPAAm-co-PAA)-block-EA-2 | NIPAAm-co-PAA3 | 64.2 | 20,400 | 1.24 |
| (NIPAAm-co-PAA)-block-EA-3 | NIPAAm-co-PAA4 | 62.5 | 46,900 | 1.40 |
| (NIPAAm-co-PAA)-block-EA-4 | NIPAAm-co-PAA4 | 45.7 | 26,400 | 1.44 |
| (NIPAAm-co-PAA)-block-EA-5 | NIPAAm-co-PAA5 | 81.3 | 30,800 | 1.26 |

[a]Polymerization was carried out at 60° C. for 24 h in EA bulk solution, AIBN as initiator and NIPAAm-co-PAA copolymer as macro-CTA.
[b]Mol fraction of poly(EA) was calculated by monomer conversions.

The micelle formation was achieved by self-association procedure. Amphiphilic block copolymer (NIPAAm-co-PAA)-block-EA was first dissolved in acetone (a suitable solvent for both block segments), followed by the slow addition of a small amount of NaOH solution to ensure the full deprotonation of PAA units. The mixture was then dialyzed against PB buffer to remove the acetone solvent.

The hydrodynamic diameters and particle size distributions of the (NIPAAm-co-PAA)-block-EA polymeric micelles in PB solution were determined by dynamic light scattering (DLS) (see Table 6). At 25° C., the intensity-average diameters of these micelles are about 30-40 nm, with narrow size distribution. The colloidal stability of these micelles is dependent on the hydrophobic/hydrophilic chain ratio. As indicated in Table 6, (NIPAAm-co-PAA)-block-EA-1, 3 and 5 block copolymers have relatively long hydrophobic pEA chains, their micelle sizes and size distribution increased upon increasing the temperature from 25 to 37° C. at pH 7.4, the temperature induced micelle aggregation or deformation takes place probably due to the loosely packed hydrophobic cores and/or the incomplete shielding hydrophobic core from hydrophilic shells, making the core accessible to the aqueous environment. In contrast, micelles from (NIPAAm-co-PAA)-block-EA-2 and 4 block copolymers with relatively short hydrophobic pEA chains are colloidally stable upon the temperature changes (Table 6). This indicates that the hydrophilic-hydrophobic balance of the a diblock copolymer plays a significant role in determining the thermodynamic stability of micelles.

Figure 15A:
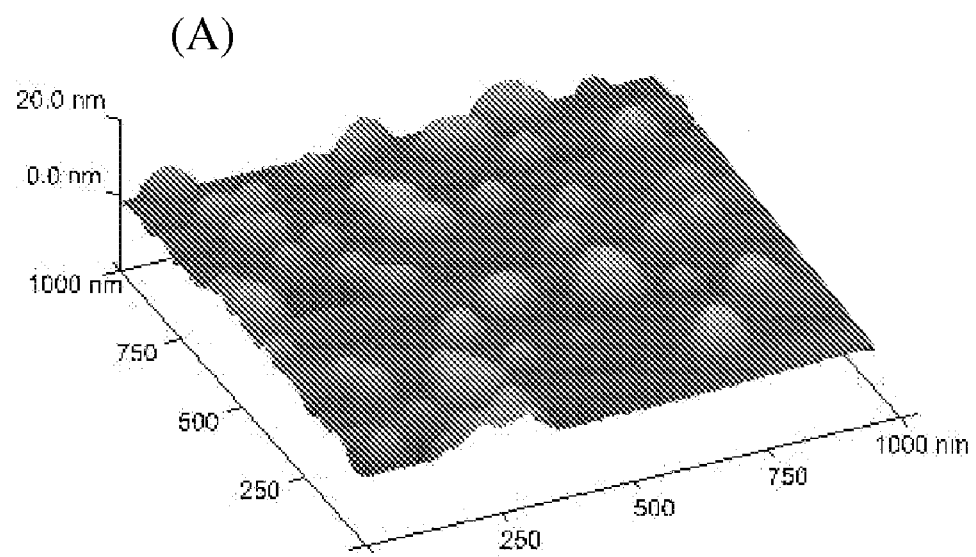
FIGS. 15A and 15B are a tapping-mode AFM image and a TEM image, respectively, of micelles from (NIPAAm-co-PAA)-block-EA-2 block copolymer. Samples were prepared by drop deposition onto freshly cleaved mica and allowed to dry in air.
Figure 15B:
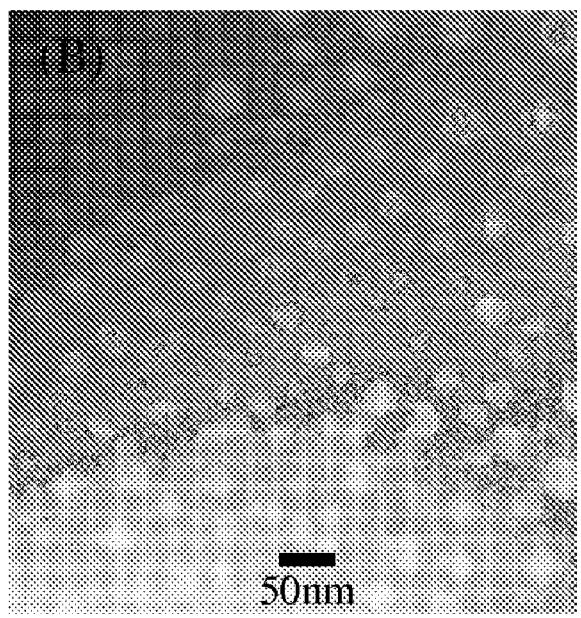

The dimensions of micelles were also characterized by tapping mode atomic force microscopy (AFM) and by transmission electron microscopy (TEM). FIGS. 15A and 15B show the typical particle images of the micelles from (NIPAAm-co-PAA)-block-EA-2 block copolymer. The diameters of the particles shown in the AFM (FIG. 15A) and TEM (FIG. 15B) images are larger than these from DLS measurements listed in Table 6. Also showed in the AFM images is that the diameter values of micelles are substantially larger than the heights. These discrepancies are due to the low $T_g$ of the pEA core allowing for the particles to be flattened during the drying process onto the solid substrate surfaces used for AFM and TEM images. The larger diameter values showed in AFM image in comparison to those in TEM image indicate greater deformation of the particles on hydrophilic mica, the substrate for AFM imaging, in comparison to the hydrophobic carbon coated grid, the substrate for TEM imaging.

TABLE 6

Characterization of (NIPAAm-co-PAA)-block-EA polymeric micelles[a]

| Block Copolymer | Micelle Diameter and (PD)[b] | | CMC[c] | LCST (° C.)[d] | |
|---|---|---|---|---|---|
| | 25° C. (nm) | 37° C. (nm) | (mg/ml) | pH 5.5 | pH 6.0 |
| NIPAAm-co-PAA-block-EA-1 | 40 ± 1 (0.17) | 94 ± 5 (0.29) | $1.0 \times 10^{-3}$ | 30.0 | 41.2 |
| NIPAAm-co-PAA-block-EA-2 | 28 ± 1 (0.09) | 29 ± 1 (0.09) | $1.1 \times 10^{-3}$ | 30.8 | 43.1 |
| NIPAAm-co-PAA-block-EA-3 | 35 ± 2 (0.03) | 88 ± 3 (0.28) | $1.4 \times 10^{-3}$ | 29.6 | 37.5 |
| NIPAAm-co-PAA-block-EA-4 | 36 ± 1 (0.07) | 33 ± 1 (0.05) | $1.7 \times 10^{-3}$ | 31.1 | 40.0 |
| NIPAAm-co-PAA-block-EA-5 | 33 ± 1 (0.07) | 208 ± 7 (0.07) | $1.3 \times 10^{-3}$ | 29.5 | 41.2 |

[a]See Table 5 for the characteristics of the diblock copolymers.
[b]Estimated by DLS; PD, polydispersity index; polymer (2.0 mg/ml) in 0.02 mol $1^{-1}$ PB buffer (pH 7.4, ionic strength = 0.15 mol $1^{-1}$); data are intensity-average diameters and recorded as the mean with standard error (n = 3).
[c]In 0.02 mol 1-1 PB buffers (pH 7.4, ionic strength 0.15 mol $1^{-1}$.
[d]Measured by the cloud point method; polymer (2.0 mg/ml) in 0.02 mol $1^{-1}$ PB buffers; The temperature at 50% light transmittance of the polymer solution was defined as the LCST.

Figure 16:
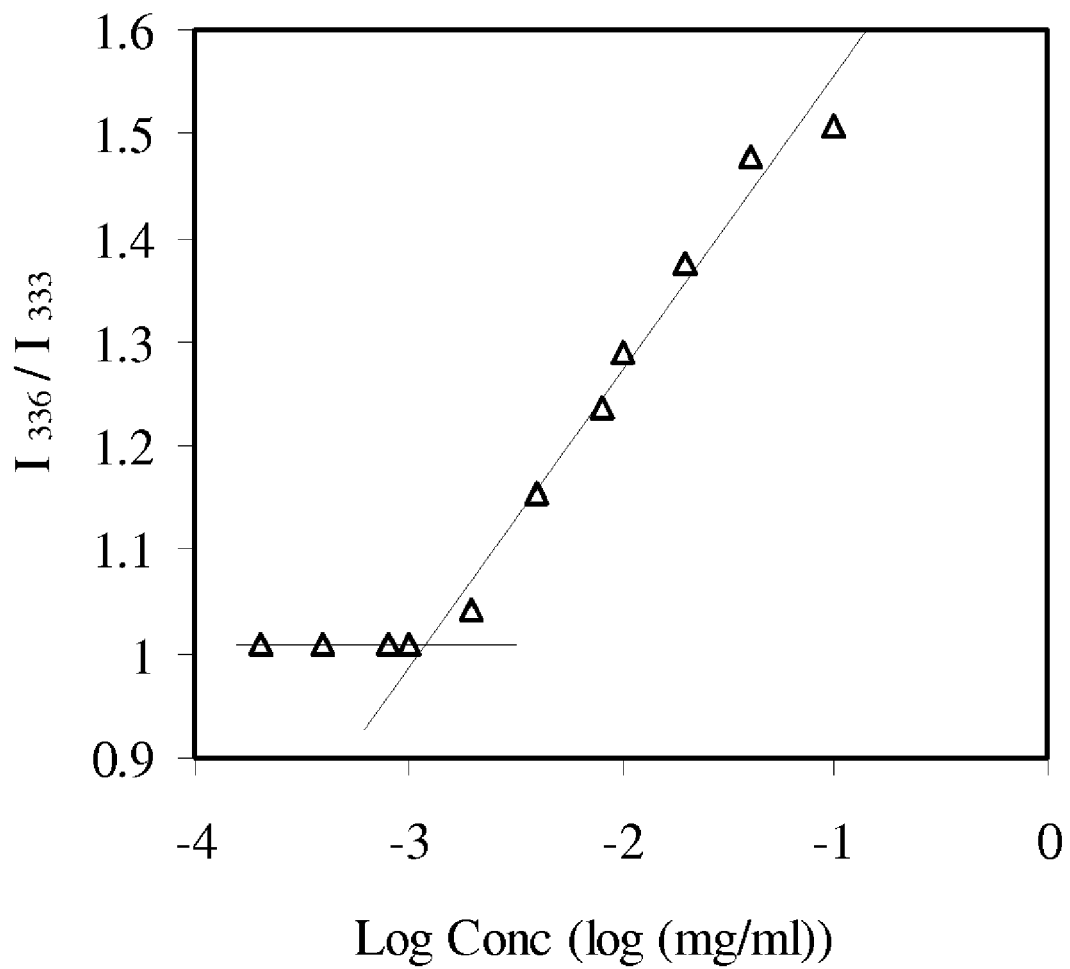
FIG. 16 is a plot of $I_{336}/I_{333}$ ratio of pyrene fluorescence intensity versus the log of concentration (mg/ml) of block copolymer (NIPAAm-co-PAA)-block-EA-2 in 0.02 mol $1^{-1}$ PB buffers (pH 7.4, ionic strength=0.15 mol $1^{-1}$). The CMC was estimated from the intersections of the horizontal line at low concentrations with the tangent of the curve at high concentrations.

The CMC values for the amphiphilic block copolymer (NIPAAm-co-PAA)-block-EA were evaluated with fluorescence spectroscopy using pyrene as a fluorescent probe. The excitation spectrum undergoes a small red shift as the pyrene probe is partitioned from a hydrophilic environment to a hydrophobic environment. The fluorescence intensities at 336 and 333 nm ($I_{336}/I_{333}$) is used to quantify such shift. FIG. 16 shows the plot of $I_{336}/I_{333}$ ratio against the log of concentration for the block copolymer (NIPAAm-co-PAA)-block-EA-2. The CMC was estimated from the intersections of the horizontal line at low concentrations with the tangent of the curve at high concentrations. The measured CMCs for the (NIPAAm-co-PAA)-block-EA block copolymers are shown in Table 6. They are in the range of 1.0-2.0 mg $1^-$. Such low CMC values indicate that (NIPAAm-co-PAA)-block-EA block copolymers form micelle at low concentrations, which is very relevant for the colloidal stability of polymeric drug carriers during their circulation in the body.

Figure 14:
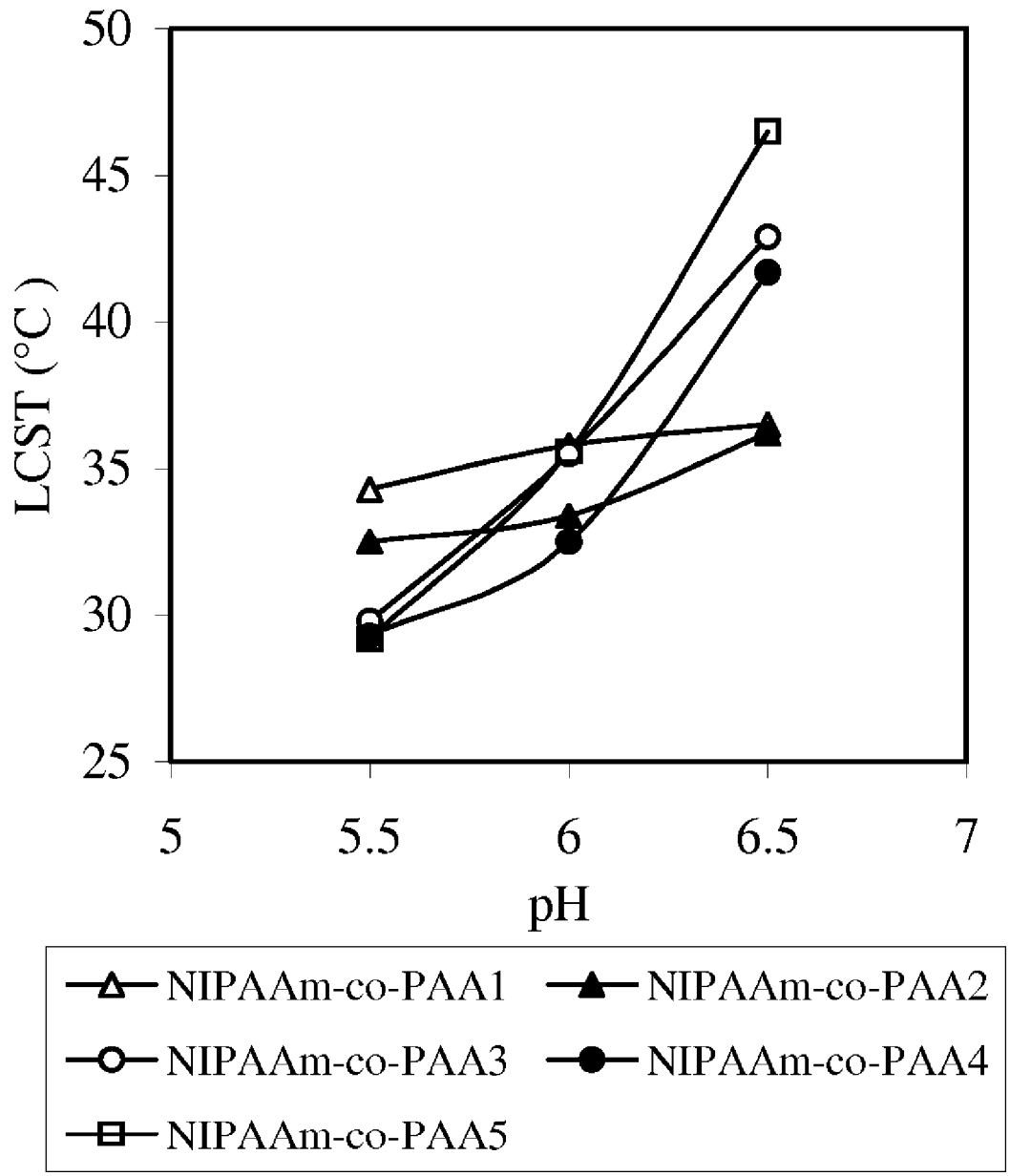
FIG. 14 is a graph illustrating LCSTs of 0.2 wt % poly(N-isopropylacrylamide-co-propylacrylic acid) (NIPAAm-co-PAA) solutions (2.0 mg/ml) with different PAA contents at different pHs as measured by the cloud point method.

To demonstrate the pH/temperature sensitivity of (NIPAAm-co-PAA)-block-EA micelles, LCSTs of micelles in PB solutions of different pHs were examined. As indicated in Table 6, the LCST values of micelles at pH 5.5 were observed to be similar to these of the corresponding building NIPAAm-co-PAA blocks (FIG. 14). It has been suggested that the hydrophobic block segments of pNIPAAm block copolymers would not influence the LCST of pNIPAAm constituent after they associate to form micelle core and get isolated from the aqueous media. As expected, LCSTs of micelles increased with increasing pH due to the deprotonation of PAA content in the shell-forming NIPAAm-co-PAA block. In addition, the LCST values of micelles at pH 6.0 (Table 6) were higher than these of the corresponding building NIPAAm-co-PAA blocks (FIG. 14). For instance, micelle from (NIPAAm-co-PAA)-block-EA-2 has an LCST of 43.1° C. at pH 6.0, while the LCST of its corresponding NIPAAm-co-PAA copolymer is 35.5° C. at the same condition. Upon ionized, the hydrophilic PAA units may interfere the hydration of hydrophobic groups of pNIPAAm more in micelles than in individual polymer due to the close packing of polymer chains in micelles.

Figure 17:
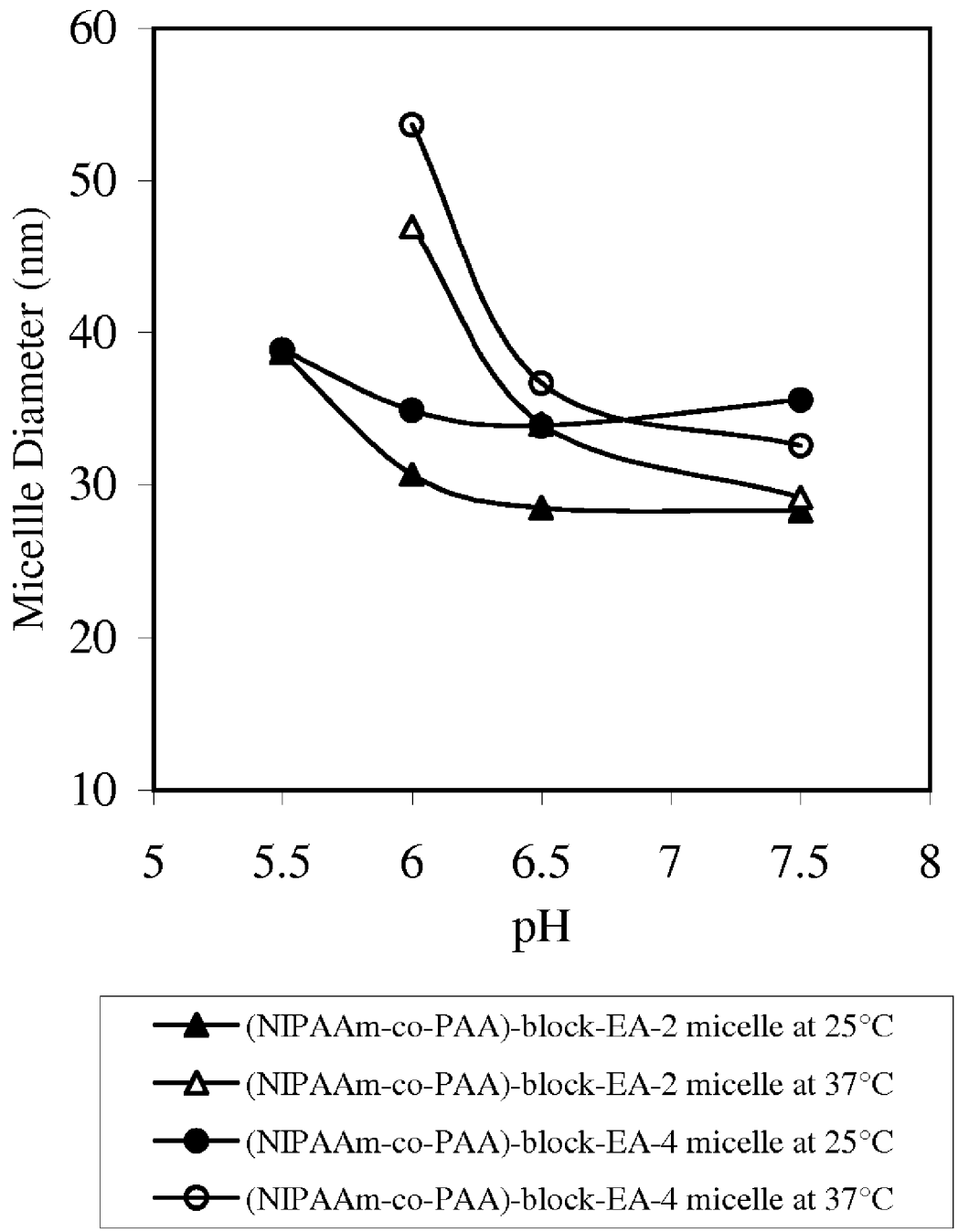
FIG. 17 is a graph of micelle diameter versus pH that shows the effects of pH on (NIPAAm-co-PAA)-block-EA micelle sizes at 25 and 37° C. as measured by DLS. The micelle diameters are indicated as intensity-average. Polymer (2.0 mg/ml) in 0.02 mol $1^{-1}$ PB buffer (ionic strength=0.15 mol $1^{-1}$)

As indicated above, (NIPAAm-co-PAA)-block-EA-2 and 4 can assemble into colloidally stable micelles at physiological conditions. The pH/temperature sensitivities of these micelles were further evaluated by following their sizes by DLS (FIG. 17). The size of the micelles was found to be pH-dependent. For instance, the particle size of micelles from (NIPAAm-co-PAA)-block-EA-2 at 37° C. is about 29.2 nm at pH 7.4, it increases to 34 nm at pH 6.5, 47 nm at pH 6.0, and polymer micelles precipitate out of the solution at pH 5.5. At pH 7.4, the PAA units are ionized, the hydrophilic shells of NIPAAm-co-PAA are very favorable with water, and the micelles are well stabilized. The hydrophilicity of NIPAAm-co-PAA shell decreases upon decreasing the pH of the aqueous media and the protonation of PAA units. The size increase could be due to the rearrangement of micelles and the increasing number of polymer chains associated in the micelles. At pH 5.5, the LCST of NIPAAm-co-PAA becomes lower than 37° C., NIPAAm-co-PAA turns hydrophobic and collapse from the solution, leading to the aggregation of polymer micelles and their precipitation out of solutions.

Temperature- and pH-sensitive diblock copolymers, for example, (NIPAAm-co-PAA)-block-EA, with various compositions were synthesized using the reversible addition fragmentation chain transfer (RAFT) polymerization method. These diblock copolymers can self-associate into micelles under relatively low critical micelle concentration (cmc, 1.0-2.0 mg $l^{-1}$), and with nano-size of about 30-40 nm and narrow size distribution. The polymeric micelles formed are stable at physiological conditions (pH 7.4, 37° C.), but deform and aggregate once a slightly acidic condition is encountered. The high sensitivity of these (NIPAAm-co-PAA)-block-EA micelles to small changes in pH indicate that they are be useful in drug delivery applications where the release of loaded drug in the micelles are triggered during the rearrangement of the micelles to aggregates and upon the precipitation of aggregates from the media.

The present invention provides stimuli-responsive polymer compositions that provide sharp and tunable responses to both temperature and pH. The polymer chains themselves can be conjugated to recognition elements such as proteins or nucleic acids to reversibly capture diagnostic targets for purification and/or concentration, or to reversibly form nanoparticles to purify and/or concentrate diagnostic targets. The polymer chains can also be used as molecular switches to provide sharp pH and/or temperature control of protein activity.

The polymer chains can also be used in stimuli-responsive drug or diagnostic reagent delivery systems, or can be crosslinked to provide stimuli-responsive hydrogels where release of reagents or drugs can be stimulated by hydration or by small changes in pH or temperature. These gels can be used for storage and release of bioanalytical reagents in diagnostic and microfluidic devices, or for controlled delivery of therapeutics.

The following examples are provided for the purpose of illustrating, not limiting the invention.

EXAMPLES

Example 1

The Preparation and Characterization of a Representative Temperature and pH-Responsive Copolymer NIPAAm-co-PAA In this example, the preparation and characterization of a representative temperature and pH-responsive copolymer of the invention, NIPAAm-co-PAA, is described.

Materials. All chemicals were purchased from Aldrich and used as received unless otherwise noted. N-Isopropylacrylamide (NIPAAm) was recrystallized from hexane prior to use. Propylacrylic acid (PAA) was synthesized according to the protocols published previously. The trithiocarbonate RAFT chain transfer agent (CTA), 2-dodecylsulfanylthiocarbonyl-sulfanyl-2-methyl propionic acid (DMP).

Polymerization. In a typical procedure, a 10 mL round-bottom flask was charged with NIPAAm (2.36 g, 20.9 mmol), PAA (0.125 g, 1.10 mmol), azobis(isobutyronitrile) (AIBN) (3 mg, $1.83 \times 10^{-5}$ mol), 2-dodecylsulfanylthiocarbonyl-sulfanyl-2-methyl propionic acid (DMP) (33.0 mg, $9.15 \times 10^{-5}$ mol) and methanol (2.50 ml, HPLC grade). The mixture was degassed by purging with nitrogen for 20 min. Polymerization was carried out at 60° C. for 17 h. After polymerization, methanol was evaporated under a stream of air at room temperature, and the polymer was dissolved in THF and precipitated twice into pentane. The final product was dried to constant weight under vacuum to provide 1.97 g of polymer (yield, 79.3%).

Characterization. Molecular weights of copolymers were determined using a gel permeation chromatograph (Viscotek), using 0.01 mol $L^{-1}$ LiBr DMF solution as eluent at a flow rate of 1 mL, $min^{-1}$ and at 60° C., and narrow disperse poly(methyl methacrylate) as calibration standards.

$^1$H NMR spectra of the copolymers were recorded on a Bruker AC 500, using methanol-$d_4$ as the solvent. Compositions of NIPAAm-co-PAA copolymers were determined by comparing the peak areas of NIPAAm unit isopropyl C—H signal at 3.9 ppm, with the total peak area between 0.8 and 1.8 ppm, which includes all other C—H protons. The degree of ionization of the copolymer at deferent pH's was determined from potentiometric titrations curves. Polymer solutions (10 mg/mL) containing 0.15 mol $L^{-1}$ NaCl at pH 12.00 was titrated with 0.1 mol $L^{-1}$ HCl to pH 2.00. The degree of ionization is defined as $\alpha = \alpha N + [H^+]/C_p$, where $\alpha_N$ is the degree of neutralization, $C_p$ is the equivalent concentration of polymer repeating units, and $[H^+]$ is proton concentration and is deducted from the pH of the solution. The titration was performed at room temperature.

LCST Measurement. The LCSTs of the polymer solutions at 0.2 wt % were measured on a Hewlett-Packard 8480A diode array UV-visible spectrophotometer by monitoring the turbidity of the polymer solutions as a function of temperature at 500 nm and under heating rate of 0.5° C./min. The temperature at 90% light transmittance of the polymer solution was defined as the LCST. NIPAAm-co-PAA copolymer was first dissolved in 0.03 mol L$^{-1}$ phosphate buffer (PB) and the ionic strength of the buffer was adjusted to 0.15 mol L$^{-1}$ by the addition of NaCl. The pH of the solution was adjusted to the desired values by adding 1 N NaOH or HCl.

Example 2

The Preparation and Characterization of a Representative Temperature and pH-Responsive Hydrogel Crosslinked NIPAAm-co-PAA In this example, the preparation and characterization of a representative temperature and pH-responsive hydrogel of the invention, crosslinked NIPAAm-co-PAA, is described.

Materials. All chemicals were purchased from Aldrich and used as received unless otherwise noted. N-Isopropylacrylamide (NIPAAm) was recrystallized from hexane prior to use. Propylacrylic acid (PAA) was synthesized according to the protocols published previously. PAA monomer was neutralized with a concentrated NaOH solution into a 34 wt % aqueous solution.

Hydrogel Synthesis. For a typical procedure, NIPAAm (475 mg), PAA (73.5 mg, 34 wt %) and N,N'-methylenebisacrylamide (MBAm, 13.6 mg) were dissolved in 4.5 mL, of deionized water. Initiator ammonium persulfate (APS; 25 µL, 10 wt %) and accelerator N,N,N'N'-tetramethylethylenediamine (TEMED; 10 µL) were mixed with the monomer solution, and the solution was quickly transferred into glass capillaries with a diameter of 1 mm. Polymerization was carried out at 4° C. overnight. The resulting hydrogel was carefully removed from glass capillaries and washed extensively in deionized water for at least 7 days. The gel rod was cut into small fragments (20 mm in length) and left to dry at room temperature for 24 h and then vacuum-dried to constant weight.

Equilibrium Swelling. The hydrogel fragments were incubated in 0.02 mol L$^{-1}$ PB buffer (ionic strength, 0.15 mol L$^{-1}$) of desired pH and temperature for 24 h in order to study their equilibrium swelling ratios. The swelling ratios were measured gravimetrically after wiping off the water on the hydrogel surface with a moistened filter paper. The swelling ratio was calculated as: Swelling ratio=$W_s/1\ W_d$, where $W_s$ is the water in the swollen hydrogel and $W_s$ is the dry weight of hydrogel.

Deswelling Kinetics. For the deswelling kinetics measurement, hydrogel fragments were first swollen in 0.02 mol L$^{-1}$ PB buffer (ionic strength, 0.15 mol L$^{-1}$) for 24 h at room temperature. The hydrogel fragments were then transferred into hot buffer solution at 35° C. quickly. The diameter of the gel, D, was measured as a function of time using a microscope with a calibrated scale. $(D_1/D_0)^3$ was used to indicate the gel swelling ratio, where $D_0$ is the diameter of gel upon preparation (1 mm).

Example 3

The Preparation of Representative Temperature and pH-Responsive Hydrogels for Therapeutic Drug or Diagnostic Agent Storage and Delivery Crosslinked NIPAAm-co-PAA In this example, the preparation a representative temperature and pH-responsive hydrogel of the invention, crosslinked NIPAAm-co-PAA, useful in therapeutic drug or diagnostic agent storage and delivery is described. In this example, the representative therapeutic drug or diagnostic agent is horseradish peroxidase conjugated rabbit anti-plasmodium aldolase or peroxidase conjugated monoclonal IgG anti-plasmodium falciparum (PfHRP2).

Materials. All chemicals were purchased from Sigma-Aldrich (St. Louis, Mo.) and used as received unless otherwise noted.

Membrane modification. Biodyne C membranes (0.45 µm pore size; Pall Corporation, East Hills, N.Y.), which have surfaces populated with reactive carboxyl groups, were exposed to a mixture of N-ethyl-N'-(3-dimethylaminopropyl) carbodiimide (EDC) and poly-L-lysine in DMF for 24 hours. The membranes were then rinsed with acetone and water and dried under vacuum. After drying, the membranes were exposed to acrylic acid N-hydroxysuccinimide in water to populate the surface with photopolymerizable vinyl groups. The membranes were rinsed again in water and dried under vacuum. Reaction efficiencies were assessed using the ninhydrin assay, which quantifies amines on surfaces.

Synthesis of pNIPAAm-co-PAA hydrogels. Polymerization of pNIPAAm-co-PAA was carried out as described above and as described by Yin et al., *Biomacromolecules* 2006 May; 7(5):1381-1385, expressly incorporated herein by reference in its entirety, yielding a 20% PAA copolymer hydrogel. The hydrogels were crosslinked to the surface of modified Biodyne C membranes by photopolymerization. NIPAAm-co-PAA, N,N'-methylenebisacrylamide (MBAm), and the photoinitiator Irgacure 2959 were dissolved in isopropanol. The solution was then transferred to the activated membrane surface and exposed to UV light for 1 hour to form a thin hydrogel layer covalently bound the membrane surface. The membrane-bound hydrogels were rinsed thoroughly in deionized water and dried under vacuum.

Protein loading and release. The hydrogels bound to modified Biodyne C membranes were cut to 6 mm circles and transferred into individual wells of a 96-well plate. The gels were then loaded with 20 µg of either Horseradish Peroxidase Conjugated Rabbit anti-Plasmodium Aldolase (ICL, Newburg, Oreg.) or Peroxidase Conjugated Monoclonal IgG anti-Plasmodium falciparum (PfHRP2; ICL, Newburg, Oreg.) in 10 µl deionized water, immediately frozen to −80° C. for 24 hours, and lyophilized. Protein release was assessed by incubation in water at either 25° C. or 45° C. At specific intervals liquid was removed and protein content quantified by BCA assay.

Assessment of protein stability. Protein stability was assessed by calorimetric ELISA. Both dried protein alone and dried protein loaded into the hydrogels were rehydrated and compared to equal amounts of protein stock stored at 4° C.

Static protein release. On average, 98.58±0.57% of the total protein loaded into pNIPAAm-co-PAA hydrogels was released within 4 min of rehydration at 25° C. (see FIG. 18), and 98.45±0.8% was released within 2 min at 45° C., demonstrating rapid recovery of reagents from immobilized hydrogels.

The ability of stored hydrogels to release active protein was also determined. Protein stability, as assessed by colorimetric ELISA, was shown to be significantly greater with proteins freeze dried within NIPAAm-co-PAA hydrogels as compared to hydrogels freeze dried with no stabilizer for up to 12 weeks of storage (see FIG. 19).

Example 4

The Preparation and Characterization of Representative Temperature- and pH-Responsive Diblock Copolymers for Polymeric Micelles for Therapeutic Drug or Diagnostic Agent Delivery (NIPAAm-co-PAA)-Block-EA In this example, the preparation and characterization of a representative temperature and pH-responsive diblock copolymer of the invention, (NIPAAm-co-PAA)-block-EA, useful making polymeric micelles for therapeutic drug or diagnostic agent delivery is described.

Materials. All chemicals were purchased from Aldrich and used as received unless otherwise noted. N-Isopropylacrylamide (NIPAAm) was recrystallized from hexane prior to use. Ethyl acrylate (EA) was passed over a basic alumina column to remove inhibitor. Propylacrylic acid (PAA) was synthesized as described in Murthy, N.; Robichaud, J. R.; Tirrell, D. A.; Stayton, P. S.; Hoffman, A. S. *J. Controlled Release* 61:137-143, 1999. The trithiocarbonate RAFT chain transfer agent (CTA), 2-dodecylsulfanylthiocarbonylsulfanyl-2-methyl propionic acid (DMP), was obtained from Noveon Company.

Synthesis of N-Isopropylacrylamide-co-Propylacrylic acid (NIPAAm-co-PAA) Copolymers. For a typical procedure, a 10 mL round-bottom flask with a magnetic stirring bar was charged with NIPAAm (1.92 g, 17.0 mmol), PAA (0.10 g, 0.88 mmol), azobis(isobutyronitrile) (AIBN) (2.6 mg, 1.58× $10^{-2}$ mmol), 2-dodecylsulfanylthiocarbonylsulfanyl-2-methyl propionic acid (DMP) (115.4 mg, 0.32 mmol) and isopropanol (2.50 ml, HPLC grade). The mixture was degassed by purging with nitrogen for 20 min. Polymerization was carried out at 60° C. for 17 h. After polymerization, isopropanol was evaporated under a stream of air at room temperature, and the polymer was dissolved in THF and precipitated twice into pentane. The final product was dried to constant weight under vacuum to provide 1.6 g of polymer (yield, 80%).

Synthesis of Poly(N-Isopropylacrylamide-co-Propylacrylic acid)-block-Poly(Ethyl acrylate) ((NIPAAm-co-PAA)-block-EA). A typical procedure for block copolymerization is as follows. NIPAAm-co-PAA copolymer macro-CTA (0.76 g, $M_n$ (GPC)=7,200, $M_w/M_n$=1.11, PAA mol %=8.5%), ethyl acrylate (EA) (3.95 ml, 36 mmol), AIBN (2.5 mg, 1.52×$10^{-2}$ mmol) and DMF (0.4 ml) were placed into a 10 ml round-bottom flask with a stir bar. The mixture was allowed to shake at room temperature for 30 min to ensure a homogeneous solution. The solution was then purged with nitrogen for 20 min. Polymerization was carried out at 60° C. for 24 h. The reaction mixture was dissolved in THF (20 ml). The resulting polymer solution was precipitated into 200 ml of methanol/water (50/50, V/V). The precipitate was recovered and dried to constant weight under vacuum at room temperature to provide 3.3 g of polymer (yield, 70%).

Characterizations of Copolymers. Molecular weights of copolymers were determined using a gel permeation chromatograph (Viscotek), using 0.01 mol $l^{-1}$ LiBr DMF solution as eluent at a flow rate of 1 ml min$^{-1}$ and at 60° C., and narrow disperse poly(methyl methacrylate) as calibration standards.

The PAA content in NIPAAm-co-PAA copolymers was measured by potentiometric titrations. Aqueous polymer solutions (10 mg/ml) at pH 12.00 were prepared and titrated with 0.1 mol $L^{-1}$ HCl to pH 2.00.

$^1$H NMR spectra of the diblock copolymers were recorded on a Bruker AC 500, using acetone-$d_6$ as the solvent.

Preparation of Polymeric Micelles. (NIPAAm-co-PAA)-block-EA block copolymer (30 mg) was dissolved in acetone (5 ml). NaOH solution (0.3 ml, 0.1 mol $l^{-1}$) was added slowly to the polymer solution. The mixture was allowed to stir at room temperature for 30 min to ensure the full deprotonation of PAA units, and was then transferred to a pre-swollen dialysis membrane tube (Spectra/Por; MWCO 12,000-14,000) and dialyzed against 0.02 mol $l^{-1}$ PB buffers (pH 5.5-7.4, ionic strength=0.15 mol $l^{-1}$) at 5° C. for 3 days (see, Costa, R. O. R.; Freitas, R. F. S. *Polymer* 2002, 43, 5879-5885, incorporated herein by reference in its entirety, describing the phase behavior of pNIPAAm in water-organic solvent mixtures. The operation conditions are important for maintaining the solvent mixture conditions for the hydrophilic block during the micelle formation). The final volume was about 10 ml, giving a polymer concentration of about 3 mg/ml. The final micelle solution was obtained after being filtered through a 0.2 μm syringe filter. The yield (wt. %) of micelles was calculated gravimetrically by lyophilizing 1 ml of micelle solutions.

Atomic Force Microscopy (AFM). Samples for atomic force microscopy (AFM) (Veeco Dimension 3100 Scanning Probe Microscope) imaging were prepared by drop depositing a diluted polymeric micelle solution (5 μl, 0.1 mg/ml in PB buffer with ionic strength=0.15 mol $l^{-1}$) onto freshly cleaved mica. The droplet was allowed to remain on the mica for 1 min before it was removed by wicking with Kimberly wiper, and the mica was allowed to dry in the air. Tapping-mode imaging was carried out with silicon probes.

Transmission Electron Microscopy (TEM). Transmission electron microscopy (TEM) images were obtained using a Philips EM420 microscope. Polymeric micelle solutions (1 ml, 0.1 mg/ml in PB buffer) were first mixed with 1 ml of 0.8 wt % phosphotungstic acid (PTA) as negative stain. The mixed solution (5 μl) was deposited onto carbon-coated copper grid. The droplet was allowed to remain on the grid for 1-2 min before it was removed by wicking with Kimberly wiper, and the copper grid was allowed to dry overnight in a cold cabinet. Micrographs were collected at 100,000× magnification.

Dynamic Light Scattering (DLS). Micelle sizes were determined by dynamic light scattering using a Brookhaven BI90Plus instrument equipped with a 535-channel correlator. A 656 nm laser source was used as the incident beam, and measurements were performed at a 90° angle. Copolymer concentrations were 2.0 mg/ml in 0.02 mol $l^{-1}$ PB buffers (pH 5.5-7.4, ionic strength=0.15 mol $l^{-1}$). Prior to analysis, solutions were double filtered through 0.2 μm nylon membrane syringe filters to remove dust particles. The incident laser intensity was adjusted to obtain a photon-counting rate between 200 to 300 kcps. Measurements were made at 25 and 37° C., respectively. For measurements at 37° C., the samples were first incubated within the temperature-controlled cuvette holder of the instrument for 20 min and size measurements were then taken 3 times every 10 min.

Fluorescence Measurement. The critical micelle concentration (CMC) of the block copolymers was determined using pyrene as a fluorescent probe as described in Wilhelm, M.; Zhao, C.; Wang, Y.; Xu, R.; Winnik, M. A. *Macromolecules* 1991, 24, 1033-1040, expressly incorporated herein by reference in its entirety. An aliquot of pyrene solution ($1.2 \times 10^{-4}$ mol $l^{-1}$ in acetone) was added into an empty glass vial, and the acetone was allowed to evaporate. Subsequently, polymer solutions (4 ml) in 0.02 mol $l^{-1}$ PB buffers (pH 7.4, ionic strength=0.15 mol $l^{-1}$) at concentrations ranging from 0.1 to $1 \times 10^{-4}$ mg/ml were added to the pyrene-containing vials. The final pyrene concentration is $6.2 \times 10^{-7}$ mol $l^{-1}$. The solutions were equilibrated for overnight at room temperature. Fluorescence measurements were taken at an emission wavelength of 395 nm and the excitation monitored from 300 to 360 nm (excitation and emission bandpass, 5 nm) using a plate reader spectrofluorometer (TECAN). The CMC was determined by plotting the intensity ratio of $I_{336}/I_{333}$ against the logarithm of polymer concentration.

LCST Measurement. The lower critical solution temperatures (LCSTs) of the polymer solutions at 2.0 mg/ml were measured on a Hewlett-Packard 8480A diode array UV-visible spectrophotometer by monitoring the turbidity of the polymer solutions as a function of temperature at 500 nm and under heating rate of 0.5° C./min. The temperature at 50% light transmittance of the polymer solution was defined as the LCST.

Example 5

The Preparation of Representative Temperature and pH-Responsive Hydrogels for Therapeutic Drug or Diagnostic Agent Storage and Delivery Trehalose-Modified Surfaces In this example, the preparation a representative temperature and pH-responsive hydrogel of the invention, crosslinked NIPAAm-co-PAA, useful in therapeutic drug or diagnostic agent storage and delivery is described. In this example, the representative therapeutic drug or diagnostic agent is horseradish peroxidase conjugated rabbit anti-plasmodium aldolase or peroxidase conjugated monoclonal IgG anti-plasmodium falciparum (PfHRP2). A representative sugar, trehalose, useful as a protein preservative is bound to the membrane to which the hydrogel is also bound.

Materials. All chemicals were purchased from Sigma-Aldrich (St. Louis, Mo.) and used as received unless otherwise noted.

Membrane modification. Biodyne C membranes (0.45 µm pore size; Pall Corporation, East Hills, N.Y.), which have surfaces populated with reactive carboxyl groups, were exposed to a mixture of N-Ethyl-N'-(3-dimethylaminopropyl)carbodiimide (EDC) and poly-L-lysine in DMF for 24 hours. The membranes were then rinsed with acetone and water and dried under vacuum. After drying, some of the membranes were further modified by exposure to acrylic acid N-hydroxysuccinimide in water to populate the surface with photopolymerizable vinyl groups. The membranes were rinsed again in water and dried under vacuum. Reaction efficiencies were assessed using the ninhydrin assay, which quantifies amines on surfaces.

Synthesis of carboxyl-modified trehalose by the Mitsunobu reaction. Trehalose dihydrate was dissolved in anhydrous dimethylformamide to which was added a 1.5 molar excess of triphenylphosphine, a 1.5 molar excess of diisopropyl azodicarboxylate, and one molar equivalent of oxalic acid. The mixture was stirred at 80° C. overnight, cooled to room temperature, and precipitated in ethyl acetate. The resulting crystals were filtered, washed with excess ethyl acetate, and dried under vacuum.

Synthesis of amine-modified trehalose by the Mitsunobu reaction. Trehalose dihydrate was dissolved in anhydrous dimethylformamide to which was added a 1.5 molar excess of triphenylphosphine, a 1.5 molar excess of diisopropyl azodicarboxylate, and one molar equivalent of sodium azide. The mixture was stirred at 80° C. overnight, cooled to room temperature, and precipitated in ethyl acetate. The resulting crystals were filtered, washed with excess ethyl acetate, and dried under vacuum.

Formation of trehalose-modified surfaces. Carboxylated trehalose was mixed with EDC and the mixture was then exposed to lysine-modified membrane surfaces for 4 hours. Amine terminated trehlose was mixed with an equimolar acryloyl-poly(ethylene glycol) N-hydroxysuccinimide ester (PEG-NHS) for 2 hours. These conjugates were transferred to the surfaces of membranes modified with photopolymerizable vinyl groups and exposed to UV light to crosslink the PEG-trehalose to the surface.

Protein loading and assessment of stability. Hydrogels bound to modified Biodyne C membranes, prepared as described in Example 3, were cut to 6 mm circles and transferred into individual wells of a 96-well plate. The gels were then loaded with 20 µg of either Horseradish Peroxidase Conjugated Rabbit anti-Plasmodium Aldolase (ICL, Newburg, Oreg.) or Peroxidase Conjugated Monoclonal IgG anti-Plasmodium falciparum (PfHRP2; ICL, Newburg, Oreg.) in 10 µl deionized water, immediately frozen to −80° C. for 24 hours, and lyophilized. Protein release was assessed by incubation in water at either 25° C. or 45° C. At specific intervals liquid was removed and protein content quantified by BCA assay. Protein stability was assessed by calorimetric ELISA. Both dried protein alone and dried protein loaded into hydrogels were rehydrated and compared to equal amounts of protein stock stored at 4° C.

Carboxyl-modified trehalose shows approximately 30% relative stability after 2 weeks of protein storage.

While illustrative embodiments have been illustrated and described, it will be appreciated that various changes can be made therein without departing from the spirit and scope of the invention.

The embodiments of the invention in which an exclusive property or privilege is claimed are defined as follows:

1. A block copolymer, comprising:
   (a) a first block comprising a random copolymer comprising:
      (i) temperature-responsive repeating units, wherein the repeating unit is an N-alkylacrylamide repeating unit; and
      (ii) pH-responsive repeating units, wherein the repeating unit is a C2-C8 alkylacrylic acid repeating unit; and
   (b) a second hydrophobic block.

2. The copolymer of claim 1, wherein the copolymer exhibits a phase transition at a pH of from about pH 5.0 to about pH 7.4.

3. The copolymer of claim 1, wherein the N-alkylacrylamide is a C3-C8 alkyl N-alkylacrylamide.

4. The copolymer of claim 1, wherein the N-alkylacrylamide is N-isopropylacrylamide.

5. The copolymer of claim 1, wherein the C2-C8 alkylacrylic acid is a C2-C8 n-alkylacrylic acid.

6. The copolymer of claim 1, wherein the C2-C8 alkylacrylic acid is selected from the group consisting of ethylacrylic acid, n-propylacrylic acid, and n-butylacrylic acid.

7. The copolymer of claim 1, wherein the C2-C8 alkylacrylic acid is n-propylacrylic acid.

8. The copolymer of claim 1, wherein the pH-responsive repeating units are present in the random copolymer in an amount from about 1 to about 20 weight percent.

9. The copolymer of claim 1, wherein the N-alkylacrylamide repeating unit is N-isopropylacrylamide and the alkylacrylic acid is propylacrylic acid.

10. The copolymer of claim 1, wherein the random copolymer has a molecular weight of from about 5,000 to about 20,000.

11. The copolymer of claim 1, wherein the block copolymer has a molecular weight of from about 15,000 to about 60,000.

12. The copolymer of claim 1, wherein the hydrophobic block is selected from the group consisting of a polystyrene, a poly(methylmethacrylate), a poly(ethylacrylate), a poly(butylacrylate), a poly(glycotide-co-lactide), and a polyoxyethylene-polyoxypropylene copolymer.

13. The copolymer of claim 1, wherein the hydrophobic block is selected from the group consisting of a poly(ethylacrylate) and a poly(butylacrylate).

14. A drug delivery device, comprising the copolymer of claim 1 and a therapeutic drug or diagnostic agent.

15. A conjugate, comprising the copolymer of claim 1 and a therapeutic drug or diagnostic agent.

16. A modified nanoparticle, comprising the copolymer of claim 1 attached to a nanoparticle.

17. The modified nanoparticle of claim 16 further comprising a therapeutic drug or diagnostic agent.

18. A micelle, comprising the copolymer of claim 1 and a therapeutic drug or diagnostic agent.

* * * * *